(12) United States Patent
Zawada et al.

(10) Patent No.: US 11,679,283 B2
(45) Date of Patent: Jun. 20, 2023

(54) ACOUSTIC DEVICE FOR SKIN TREATMENT AND METHODS OF USING THE SAME

(71) Applicant: TOOSONIX A/S, Hoersholm (DK)

(72) Inventors: Tomasz Zawada, Hoersholm (DK); Torsten Bove, Hoersholm (DK)

(73) Assignee: Toosonix A/S, Hoersholm (DK)

( * ) Notice: Subject to any disclaimer, the term of this patent is extended or adjusted under 35 U.S.C. 154(b) by 0 days.

(21) Appl. No.: 17/380,726

(22) Filed: Jul. 20, 2021

(65) Prior Publication Data
US 2022/0008752 A1    Jan. 13, 2022

Related U.S. Application Data

(63) Continuation of application No. 16/349,249, filed as application No. PCT/EP2018/055015 on Mar. 1, 2018, now Pat. No. 11,491,351.

(60) Provisional application No. 62/542,217, filed on Aug. 7, 2017, provisional application No. 62/541,634, filed on Aug. 4, 2017, provisional application No. 62/465,742, filed on Mar. 1, 2017.

(51) Int. Cl.
*A61N 7/00* (2006.01)
*A61N 7/02* (2006.01)
*A61B 90/00* (2016.01)
A61B 17/00 (2006.01)
A61B 34/10 (2016.01)

(52) U.S. Cl.
CPC .............. *A61N 7/00* (2013.01); *A61B 90/361* (2016.02); *A61N 7/02* (2013.01); *A61B 34/10* (2016.02); *A61B 2017/00769* (2013.01); *A61N 2007/0034* (2013.01); *A61N 2007/0056* (2013.01); *A61N 2007/0065* (2013.01); *A61N 2007/0082* (2013.01)

(58) Field of Classification Search
None
See application file for complete search history.

(56) References Cited

U.S. PATENT DOCUMENTS

| | | | |
|---|---|---|---|
| 2007/0106349 A1* | 5/2007 | Karni | A61B 18/042 607/101 |
| 2013/0141179 A1* | 6/2013 | Chen | H03B 5/364 331/158 |
| 2014/0276055 A1* | 9/2014 | Barthe | A61B 8/4466 600/439 |

OTHER PUBLICATIONS

Theory of Focusing Radiators by H. T. O'Neil, pub. The Journal of the Acoustical Society of America vol. 21, No. 5 Sep. 1949, pp. 516-526 (Year: 1949).*

(Continued)

*Primary Examiner* — Christopher Koharski
*Assistant Examiner* — Michael S Kellogg
(74) *Attorney, Agent, or Firm* — Orbit IP, LLP

(57) ABSTRACT

Methods of treating the skin and in particular removing pigment from a tattoo are provided. In preferred embodiments, a piezoelectric transducer is placed at a plurality of locations above the skin and focused acoustic waves at 7 MHz or more are transmitted into the skin. The focal point of the focused acoustic waves is between 0.1 mm and 5 mm below the surface of the skin. The design of the piezoelectric transducer along with the frequency of operation are carefully chosen to create points of treatment with a desired size and shape. The correct amount of energy is supplied to the points of treatment to produce a lesion of a desired size and shape. The lesions are spaced and located to effect the treatment of the skin.

18 Claims, 26 Drawing Sheets

(56) References Cited

OTHER PUBLICATIONS

Y. Sun et al., "Development of a multi-modal tissue diagnostic system combining high frequency ultrasound and photoacoustic imaging with lifetime fluorescence spectroscopy," 2008 IEEE Ultrasonics Symposium, 2008, pp. 570-573, doi: 10.1109/ULTSYM.2008.0137. (Year: 2008).*

* cited by examiner

ACOUSTIC DEVICE FOR SKIN TREATMENT AND METHODS OF USING THE SAME

CROSS REFERENCE TO RELATED APPLICATIONS

This patent application is a continuation of U.S. application Ser. No. 16/349,249, filed May 10, 2019, which is a U.S. National Stage entry of International Application No.: PCT/EP2018/055015, filed Mar. 1, 2018, which claims the benefit of U.S. Provisional Patent Application No. 62/465,742, filed Mar. 1, 2017, U.S. Provisional Patent Application No. 62/541,634, filed Aug. 4, 2017, and U.S. Provisional Patent Application No. 62/542,217, filed Aug. 7, 2017, which are all hereby incorporated by reference in their entirety.

FIELD

This patent document relates to acoustic devices and their use in methods and systems for treatment of the skin. In particular this patent document relates to the use of acoustic devices for the removal of tattoos from the human dermis and epidermis.

BACKGROUND

FIG. 1 illustrates the basic physiology of human skin 6. Human skin 6 is composed of an outer epidermis-layer 1, which is separated by the basement membrane 2 towards the deeper dermis 3 layer and even deeper subcutaneous layer 4.

Throughout the dermis 3 and subcutaneous 4 layers, lymphatic channels 5 provide transport of nutrients, cells and various pathogens to and from the skin 6. The transport of dead cells away from the dermis-layer 3 is facilitated by macrophages, which are a type of white blood cell. In a process called phagocytosis, the macrophages engulf and digest cellular debris, foreign substances, microbes, cancer cells, and anything else that does not have the types of proteins specific of healthy body cells on its surface.

The basement membrane 2 controls the traffic of the liquid, molecules and cells between the dermis 3 and epidermis 1, but also serves as a reservoir for their controlled release during physiological remodelling or repair processes. As the epidermis 1 contains no blood vessels, transport through the basement membrane 2 to the epidermis 1 is limited by the diffusion-processes, which thereby also effectively limits transport of larger particles, cells or chemicals, such as pigments, through this barrier. The thickness of the above-mentioned three outer layers of the skin is typically in the range of 0.1 mm to 5.0 mm depending on the location on the body.

A typical tattoo procedure involves the deposition of pigment particles into the dermis 3 by a large number of physical punctures. This results in tattoo pigment particles residing at depths from 0.1 mm down to approximately 4 mm from the surface of the skin. In some extreme cases, the pigment is injected into deeper layers up to 10 mm. A significant amount of the deposited pigments will quickly be removed by phagocytosis and transported through the punctured basement membrane. It has been estimated that up to two-thirds of the initially deposited pigment-particles are transported away through phagocytosis. The transported pigment can be seen in the discoloration of the lymph nodes, which are the initial waste deposit sites in the body's immune system.

As illustrated in FIG. 2, the remaining pigments 7 that could not be transported away immediately through the epidermis 1 or through the dermis 3 by the lymphatic system, are concentrated as the permanently visible tattoo in the upper layer of the dermis 3 blocked from further mobility towards the epidermis by the basement membrane 2.

Nowadays, due to cultural and fashion related reasons, tattooing is a very popular procedure. This also results in a large population of people that, for medical and non-medical reasons, are interested in tattoo removal. Depending on the country, it is estimated that between 5% and 15% of the tattooed population is considering having a tattoo removed. Hence the need for more efficient and less painful tattoo removal techniques and methods.

Non-acoustic methods of tattoo removal are known in the art. Non-acoustic Tattoo removal techniques can broadly be divided into three approaches: mechanical, chemical and selective.

Mechanical methods involve physical elimination of the pigment from the tissue, by methods such as dermabrasion, excision, or grafting. Such surgical/excisional techniques may be appropriate for small tattoos and when no other methods are possible due to medical considerations.

Several chemical methods have also been used, either in conjunction with dermabrasion, or as a stand-alone therapy. The treatments involve injection of various chemicals into the tattooed skin, in some cases in conjunction with flushing and/or pumping. Some treatments involve tannic or lactic acid and silver nitrate, while phenol and trichloroacetic acid peels are also still in use.

With the invention of Q-switched lasers in the late 1960s, the outcomes and availability of tattoo removal changed radically. The modern laser-method tattoo removal techniques use localized heating. The laser-induced injuries are confined to microscopic targets if there is selective light absorption in the target and not in the surrounding structures, and if the light is delivered and absorbed within a period of time shorter than—or equal to—the time needed for the target to transfer the absorbed energy to surrounding structures. Tattoo pigment particles in the skin will absorb laser-light, provided it is of the correct wavelength, and quickly transform it to significant local heating. Temperatures up to 900° C. have been reported. The very quick heating leads to sudden thermoplastic expansion, accompanied by shock-waves, cavitation, and mechanical shear stresses vastly above the yield stress of the pigment particles and pigment containing cells. The pigment particles and pigment containing cells therefore scatter into much smaller fragments. In the days and weeks following treatment, the skin will become inflamed due to the immune response spread across the pigments and debris from the fragmented cells in the phagocytosis-process. This process of inflammation and phagocytosis clears a portion of the tattoo pigment from the dermis via transport through the lymphatic system.

Laser based methods and procedures typically involve use of monochromatic light that may not be absorbed with equal effectiveness by different colours in the tattoo. Several repeated treatments with varying laser-sources are therefore often required to fully remove all colours in a tattoo. It is, for example, reported that black pigments are best removed by lasers using 1064 nm wavelength, blue and green pigments using 694 nm or 755 nm, and red pigments using 532 nm. White and yellow pigments are inherently difficult to remove due to their high reflection of the incoming laser light.

For all the above-described methods, significant adverse effects have been reported. The mechanical and chemical methods are by their invasive nature subject to pain, frequent scarring, infection and change in pigmentation. The laser-method is also reported to be extremely painful, and often leads to significant blistering due to local heating of the tissue. This in turn leads to risk for infection and scars as a secondary effect during the healing period.

Permanent pigment darkening is another frequently reported side effect from laser treatment. This phenomenon is a risk particularly in removal of white, pink and red pigments. The darkening is explained by a reduction of metallic oxide in the pigment (e.g. $Fe_2O_3$, which has a reddish hue, to the black ferrous oxide FeO). A similar reaction occurs when titanium dioxide, used in white dyes or mixed with bright colours to enhance the brilliance of tattoos, is exposed to laser light. These reactions are pure chemical transformations induced by absorption of the laser by the metallic oxide and cannot be reversed or decreased by repeated laser treatment.

Since the laser light used in laser-based tattoo removal is also absorbed by melanin in the skin, pigmentary change, both hyperpigmentation and hypopigmentation, is a common adverse effect. Pigment changes are most predominant with the wavelengths used for removal of blue and green pigments.

Another frequent side effect from laser-based tattoo removal is scarring following treatment of multi-layered tattoos. Many people apply a second camouflage tattoo ('retattoo') over an undesired first tattoo. However, when the final tattoo outcome is not desirable, and the patient seeks removal of the entire tattoo composition, they may forget to report a prior underlying tattoo. The scarring phenomenon is often more severe in multiple tattoo locations. This is likely due to the high density of pigment in these layered tattoos, which causes a very strong absorption of energy. The additional energy absorption produces heat so intense that it causes damage even to the surrounding dermis.

Equally important to the above visible side effects, is the fact that the high energy generated by lasers for tattoo removal can cause in-vivo reactions to certain chemicals used in the inks and pigments. This leads to an increased risk for allergic reactions and serious long-term effects from unknown and uncontrolled reactants generated by the process. High laser intensities are, for example, known to cleave the azo compounds used in many red tattoo pigments, leading to an increase in decomposition products such as 2-methyl-5-nitroaniline, 2- to 5-dichloraniline, and 4-nitrotoluene, which are toxic and potentially carcinogenic compounds.

Recently, alternative methods for selective tattoo removal have been reported. It has been proposed that one can overcome the aforementioned drawbacks by utilizing an acoustic energy treatment. Such a method for acoustic treatment of tissues for tattoo removal can be non-invasive. The method can include directing acoustic energy deposition into a tissue by creating an energy distribution function. The energy distribution function is assumed to be tuned to control treatment of a target zone within the dermis, pigment particle or agglomerates thereof embedded in the dermis, or any combination thereof to remove at least a portion of a tattoo.

In one research report entitled "Ultrasound: An alternative solution for removing tattoos" by Jennifer Teng, published by MIT in 2005, focused ultrasound was used to investigate an acoustic energy treatment by studying the effect of focusing ultrasound at 7.5 and 10 MHz into a skin-phantom containing glass- or polystyrene particles. Because the applied ultrasound frequency had a maximum setting of 10 MHz, only particles of 50 microns or greater were of specific interest. Based on frequency calculations, these particle sizes were expected to exhibit the greatest potential to be fractured by the ultrasound treatments. However, this size range should be compared to tattoo inks, which are suspensions of insoluble, coloured microparticles ranging from only about 0.1 to 10 microns in diameter.

The report assumes that dermal cells consume and store tattoo particles in vacuoles in the same manner fat cell store lipids. It is therefore assumed that tattooed cells adopt an "effective density" analogous to the way fat cells develop a lower density. These cells may be selectively disrupted based on differences in mechanical and acoustic properties between healthy and tattooed cells. It is hypothesized that focused, high frequency ultrasound can be used to selectively target ink containing cells in the dermis.

The results of both experiments included successful mechanical disruption of the tested glass and polystyrene beads, although the extent of the observed effects was primarily bound to the large treated particle size.

In a recent patent application, numbered WO 2015/200762 A1 and titled "Methods and systems for tattoo removal", a very similar method is proposed. It is proposed that stresses created by inducing an acoustic-mechanical or acoustic-elastic effect in a pigment particle or agglomerate can exceed a fragmentation threshold of the pigment or agglomerate. The method can include one or more of the following steps: coupling an ultrasound energy source to the pigment particle or agglomerate thereof embedded in the dermis; and initiating, using a single ultrasound energy pulse from the ultrasound energy source, an acousto-mechanical or acousto-elastic effect in the pigment particle or agglomerate thereof that exceeds a fragmentation threshold of the pigment particle or agglomerate thereof and can fragment the pigment particles or agglomerates thereof into a plurality of sub-particles of a size that can initiate an immune response which can remove the pigment sub-particles, thereby removing a portion of the tattoo. The term "fragmentation threshold" refers to the minimum amount of energy directed at an object in a region of interest which causes the object to fragment.

Both of the above-mentioned ultrasound-based methods propose a potential alternative to the currently dominating laser-based tattoo removal. By using ultrasound, it is hypothesized that it may be possible to avoid many of the adverse effects of micro-surgery and laser-based methods, that are often painful and produce hypopigmentation and permanent thermal skin damage. The proposed methods focus on the effect of directing ultrasound energy from the ultrasound energy source into the pigment particle or agglomerate thereof. The methods however do not effectively address or demonstrate methods or functionalities to effectively do so on individual cells, pigments and agglomerates in the relevant size-range below 10 μm in diameter.

If the wavelength from the ultrasound energy source is too large, a particle caught in either a positive or negative wave will not receive enough stress and strain in order to achieve mechanical disruption. Simultaneously, if a wavelength is too high, there may be too much disruption in the targeted area resulting in damaged healthy cells as well as greater thermal buildup (frequency has a positive correlation with temperature increases). As a result, in order to obtain the proposed acousto-mechanical or acousto-elastic effect on individual cells, pigments and agglomerates thereof in in a size-range below 10 μm, a wavelength around two times this value has to be used. This means that the ultrasound energy source must operate at frequencies in the range of 50 MHz to 100 MHz to be effective in transferring stresses to individual particles. Systems operating at such high frequencies are known to be inherently difficult and expensive to manufacture, and have significant limitations in the possible penetration depth into human skin or other media due to the frequency-dependent attenuation of propagating ultrasound waves According to the above, it would therefore be useful to demonstrate a new, better and more practical technique for ultrasound-based tattoo removal that is non-invasive, less painful, cheaper, have fewer side-effects, and are not limited to certain pigment colours.

SUMMARY OF THE EMBODIMENTS

Objects of the present patent document are to provide an improved apparatus and methods for the treatment of skin and for tattoo removal. The embodiments herein use acoustic energy in a controlled manner not taught by the prior art. In particular, the embodiments herein control the delivery of the acoustic energy to much smaller volumes than previously thought possible with a higher degree of accuracy. This is achieved through a combination of piezoelectric transducer design and power control. The size and location of the resulting lesions in the skin produce the bodies most effective responses for the removal of unwanted particles in the skin, including tattoo pigments. At the same time, pain during the procedure and scaring after the procedure are both greatly reduced.

To this end, in one embodiment, an ultrasonic device is provided. In a preferred embodiment, the ultrasonic device comprises: a hand-piece with a focused acoustic element together with an appropriate impedance matching circuit (the transducer). The impedance matching circuit is connected to the power unit and in some embodiments, comprises a control module, signal generator, and power amplifier. In operation, the transducer is brought into physical contact with skin above a selected point of treatment (PoT) by use of a coupling media (e.g. water or ultrasonic gel). In some embodiments, the skin above the PoT is clearly monitored and visualized by an optical camera integrated into the handpiece and transmitting images to an internal or external screen. The coupling media provides mechanical and acoustic matching to the skin, thus providing an efficient ultrasonic energy transmission into the skin. The focused transducer transmits a signal of pre-defined frequency, pulse duration and intensity into a well-defined focal point inside the PoT, which creates a lesion. Since the lesions are created by mechanical energy, they are independent of Fitzpatrick skin type, pigment colour, or pigment concentration, as opposed to laser treatment relying on absorption of electromagnetic energy.

The lesion will initiate an immune-response, which will partly remove pigment-containing cells and individual pigment particles through three different mechanisms: 1) expelling material through the epidermis; 2) phagocytosis that eventually transports the pigment away through the lymphatic system; and 3) Creating volumes in the skin that will gradually excrete well-defined sections of dermis and epidermis containing a high concentrations of tattoo pigments.

In one aspect of the teachings herein, a method of treating skin is provided. In preferred embodiments, the method comprises placing a piezoelectric transducer at a first location above the skin; transmitting focused acoustic waves from the piezoelectric transducer into the skin to create a point of treatment wherein the focused acoustic waves have a 6 dB focal zone with a focal diameter of less than 1.5 mm and a depth of focus of less than 3.0 mm; and moving the piezoelectric transducer along the surface of the skin to a second location 5 mm or less from the first location and repeating the transmitting step.

In some embodiments, the focal zone may be even more tightly controlled and may have a focal diameter of 500 µm or less and a depth of focus of 1.5 mm or less. Other embodiments may have a focal diameter of 100 µm or less and a depth of focus of 500 µm or less. In yet other embodiments, the focal zone may be even more tightly controlled and may have a focal diameter of 80 µm, 50 µm or even 40 µm or less and a depth of focus of 400 µm, 300 µm or even 250 µm or less.

During treatment, the amount of energy delivered to the point of treatment is controlled to result in a lesion of the current size. In some embodiments, 10 Watts or less of acoustic power is transmitted to the point of treatment for 100 ms or less. This is only a single power and time setting and many other power and time settings are possible. As taught herein, the amount of energy delivered to the point of treatment may be coordinated with the controlled size of the focal zone to produce an exacting response.

As explained in more detail below, in order to deliver acoustic energy more precisely to effect treatment, the piezoelectric transducer needs to be designed accordingly. In some embodiments, the piezoelectric element is in the shape of a focusing bowl with a thickness 0.1 mm or greater. Because producing piezoelectric elements in the 0.1 to 0.2 mm range can be expensive, the preferred embodiments use piezoelectric elements with a thickness of 0.2 mm or greater.

In some embodiments, the piezoelectric element is operated at a higher harmonic resonance frequency. The higher harmonic frequency is preferably the third harmonic frequency but may be the fifth, seventh or ninth or more.

As taught herein, using higher order harmonics will allow the piezoelectric element to operate at higher frequencies at thicker cross-sections. Because incredibly thin elements are difficult and expensive to manufacture and also hard to work with, this is a big advantage. Accordingly, in some methods, the piezoelectric transducer is operated at a frequency of 7 Mhz or more. In other embodiments, the piezoelectric transducer is operated at 20 MHz, 30 MHz or 50 MHz or more.

The focal point of the piezoelectric transducer is about 0.1 mm to about 10 mm below the surface of the skin. However, in preferred embodiments, the focal point is 1±0.2 mm below the surface of the skin.

Although the methods taught herein may be used for any type of treatment of the skin, the methods are preferably used for tattoo removal. Accordingly, locations of treatment may be within a tattoo.

The focused acoustic energy is controlled to induce the body to create lesions. At the points of treatment lesions are preferably formed. The lesions may span between the dermis and epidermis layers of the skin and puncture the basement layer of the skin.

In preferred embodiments, the process is sufficiently repeated to create an area of lesions that causes expulsion of pigment through a basement membrane of the skin, removal of pigment by a lymphatic system and separation and excretion of the area of lesions.

Other methods of treating skin taught herein comprise: placing a piezoelectric transducer at a first location above the skin; transmitting focused acoustic waves from the piezoelectric transducer into the skin to create a point of treatment wherein the point of treatment is defined by a volume that experiences an acoustic intensity of 100 W/m2 or more and the point of treatment is confined to a diameter of 2 mm or less in the X-Y plane where the Z-axis is into and out of a surface of the skin; and moving the piezoelectric transducer along the surface of the skin to a second location 5 mm or less from the first location and repeating the transmitting step.

In some embodiments, the surface of the skin above the point of treatment is optically observed through a hole in the piezoelectric transducer. To this end, in another aspect of the teachings herein, an acoustic device for treatment of the skin is provided. Preferably, the acoustic device comprises a housing with a first end; an acoustic generating device with a hole wherein the acoustic generating device is coupled to the housing and wherein the acoustic device focuses acoustic waves generated by the acoustic generating device to a point of treatment that is outside the housing past the first end; an axis through the point of treatment and a center of the hole; electronics designed to drive the acoustic generating device coupled to the housing and in electrical communication with the acoustic generating device; and an optical monitoring system located on an opposite side of the acoustic generating device from the first end with an optical axis aligned with the axis such that the optical monitoring system looks through the hole towards the first end. In preferred embodiments, the hole is in the center of the acoustic generating device.

The acoustic device may also include a cavity in the housing between the acoustic generating device and the first end wherein the cavity contains a coupling medium. In preferred embodiments, the coupling medium is water. The housing may have a hole in the first end that is covered by a coupling window. The coupling window prevents the coupling medium from escaping from the cavity.

In some embodiments, the acoustic device further comprises a light source. The light source may be one or more light emitting diode and may protrude through a wall of the cavity. In some embodiments, two light emitting diodes may be used.

Preferably, the housing comprises a first housing and a second housing coupled together but selectively detachable and wherein the acoustic generating device and electronics are both coupled to the second housing to form a transducer head that is selectively detachable from the first housing. In addition, a power supply and the optical monitoring system may be coupled to the first housing.

In yet other embodiments, an acoustic device for treatment of the skin is provided that comprises: a housing with a first end and a cavity located in the first end wherein the first end has a hole that extends into the cavity; a disk shaped piezoelectric element designed to transmit acoustic waves and coupled to the housing in the cavity opposite the first end; an acoustic window covering the hole; a coupling medium filling the cavity.

In another aspect of the teachings herein, a process of removing a tattoo is provided. The process comprises: positioning a piezoelectric element shaped to emit a focused set of acoustic waves above a tattoo; imaging an area of the tattoo up through a hole in the center of the piezoelectric element; adjusting the position of the piezoelectric element based on the image; and causing the piezoelectric element to emit the focused set of acoustic waves.

In still yet other embodiments, an acoustic device for treatment of the skin is provided that comprises: a hand-held device including a first housing section and a second housing section wherein the first housing section is selectively coupled to the second housing section; an acoustic wave generator coupled to the first housing section; electronics designed to drive the acoustic wave generator coupled to the first housing section and in electrical communication with the acoustic wave generator; an optical monitoring assembly coupled to the second housing section; a power supply coupled to the second housing section; and wherein the first housing section, acoustic wave generator and electronics form a transducer head that may be selectively detached from the hand-held device.

Methods of treating the skin are further provided that comprise: positioning a piezoelectric element shaped to emit acoustic waves focussed to a point of treatment below the surface of a patient's skin; causing the piezoelectric element to emit the acoustic waves; forming a lesion of a fixed size and volume that pierces the basement layer and spans between the dermis and epidermis; and repeating the positioning, causing and forming steps at a second location The embodiments described herein may be used to remove or lighten a tattoo depending on the nature of the tattoo and on the number of repeated treatments performed. The embodiments may be used either as a stand-alone treatment or in combination with other treatment types such as laser removal or various chemical treatments.

Further aspects, objects, desirable features, and advantages of the apparatus and methods disclosed herein will be better understood from the detailed description and drawings that follow in which various embodiments are illustrated by way of example. It is to be expressly understood, however, that the drawings are for the purpose of illustration only and are not intended as a definition of the limits of the claimed embodiments.

DETAILED DESCRIPTION OF THE PREFERRED EMBODIMENTS

The detailed description that follows teaches methods, systems and apparatus for the treatment of skin. In particular, methods systems and apparatus are described that use focused acoustic energy to create lesions in the various layers of skin. Although one primary purpose of the methods, systems and apparatus taught herein is the removal of tattoos, one skilled in the art will appreciate that those same methods, systems and apparatus may have many applications. As just a couple examples, the methods, apparatus and systems taught herein can be used for other skin treatments like wart removal and even for non-skin treatments.

Figure 1:
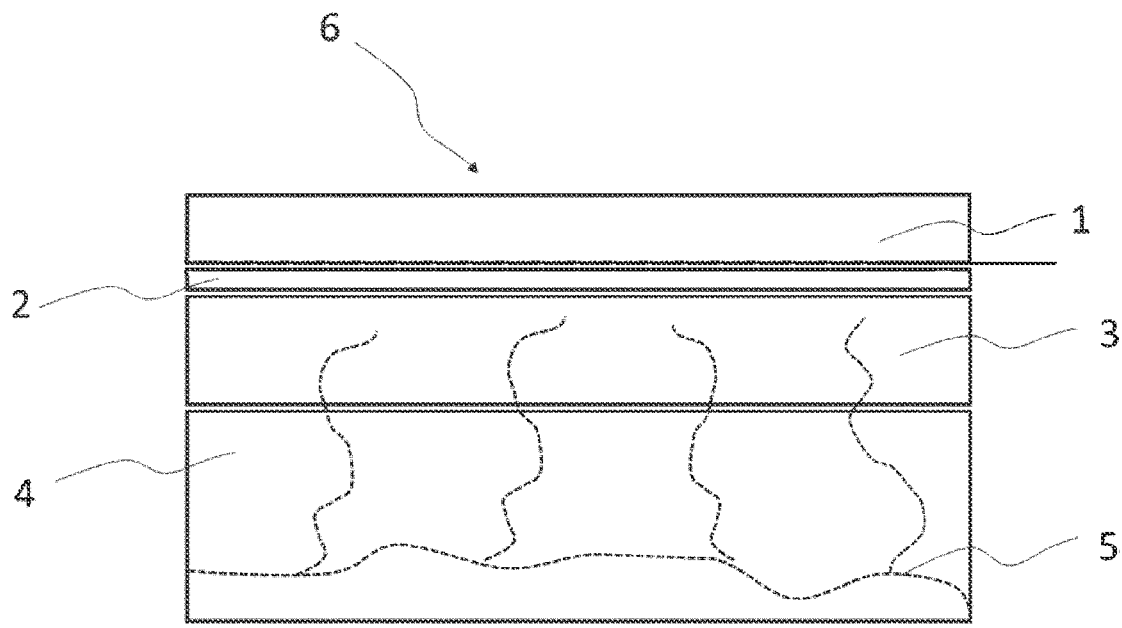
FIG. 1 illustrates a cross-section of the schematic structure of the human skin.

FIG. 1 illustrates a cross-section of the schematic structure of the human skin. 6 comprising epidermis 1 at the surface, the basement membrane 2, dermis 3, and the deeper subcutaneous tissues 4. A network of lymphatic capillaries 5 connects the dermis 3 to the deeper lymphatic system 4.

Figure 2:
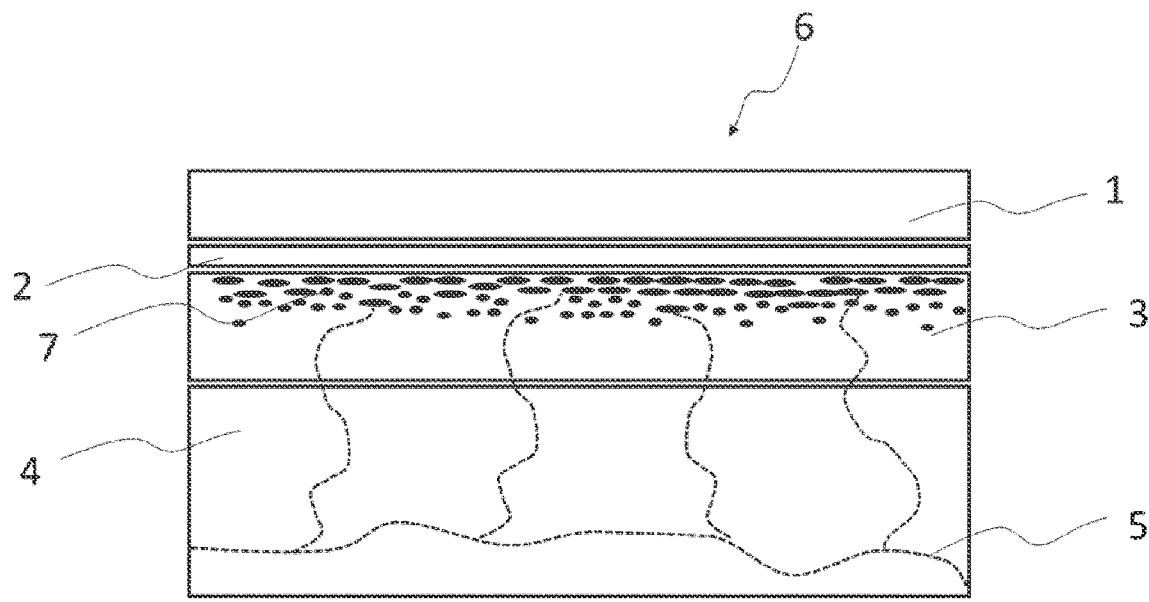
FIG. 2 illustrates a cross-section of skin with the location of the permanently visible tattoo-pigments shown in the skin.

FIG. 2 illustrates a cross-section of skin 6 with the location of the permanently visible tattoo-pigments 7 shown in the skin 6. The pigments 7 are typically concentrated in the upper layer of the dermis 3 and blocked from further transport to the epidermis 1 by the basement membrane 2.

Figure 3:
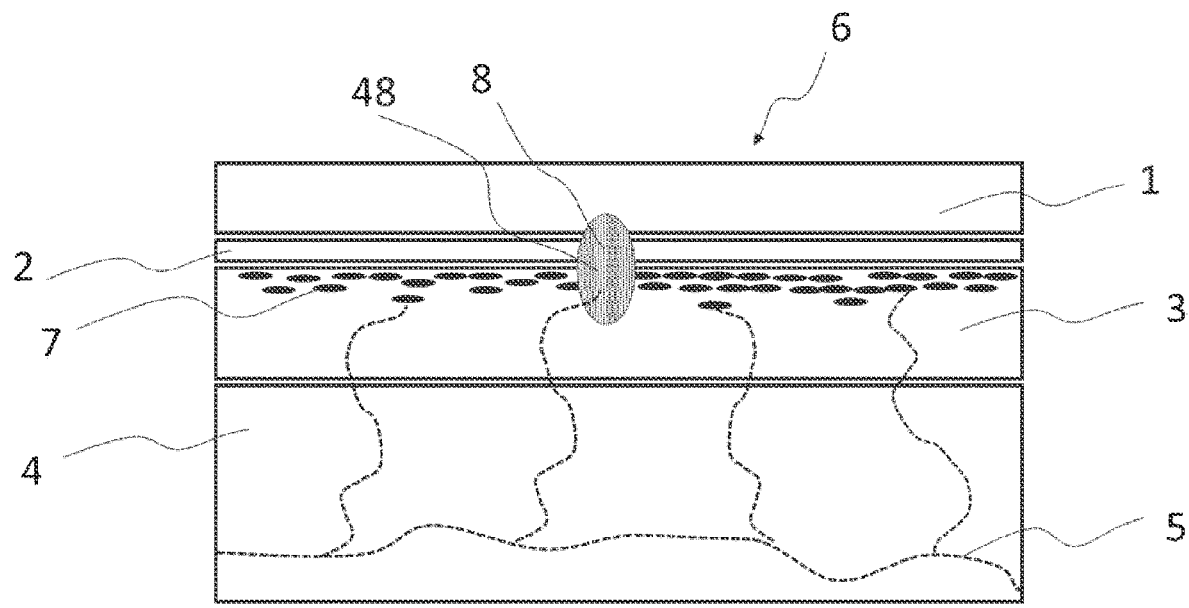
FIG. 3 illustrates a cross section of skin with a small lesion created at the PoT located in the interface between dermis and epidermis.

FIG. 3 illustrates a cross section of skin 6 with a small lesion 48 created at the Point of Treatment ("PoT") 8 between dermis 2 and epidermis 1 and through the basement layer 2. As used herein, the term "lesion" refers to a volume of tissue in the epidermis layer 1, dermis layer 3, and/or subcutaneous layer 4, that has been modified by focused ultrasound energy (coagulated, denaturated, ablated etc.) as depicted in FIG. 3. In the applications described herein, lesions 48 are the consequence of thermal heating, and/or cavitation caused by an acoustic intensity of above 1000 W/cm$^2$. During thermal heating, a volume of tissue within a lesion 48 may be heated to temperatures well above 42° C.

In the present patent document, the location of the lesion 48 is referred to as the Point of Treatment (PoT) 8. Creating a lesion 48 may be thought of as the first step in the basic functionality of the treatment methods described herein. One advantage to the methods taught herein is that the size and location of the PoT may be precisely controlled. Because the size and location of the lesion 48 directly corresponds to the size and location of the PoT, the methods taught herein can place the lesions precisely where they are needed. In contrast, previous methods or apparatuses for skin treatments and tattoo removal primarily address individual pigments and agglomerates thereof in the three outer layers of the skin 6 (Dermis, Basement Membrane and Epidermis), rather than generic volumes. To this end, the methods, apparatus and systems taught herein have a distinct advantage over previous methods, apparatus and systems.

As illustrated in FIG. 3, the PoT 8 and consequently the lesion 48, may be created centred in the dermis layer 3 and extending through the basement membrane 2 outwards into the epidermis layer 1. The punctured basement membrane will allow pigment particles and pigment-containing cells to be expelled into the epidermis layer.

Figure 4:
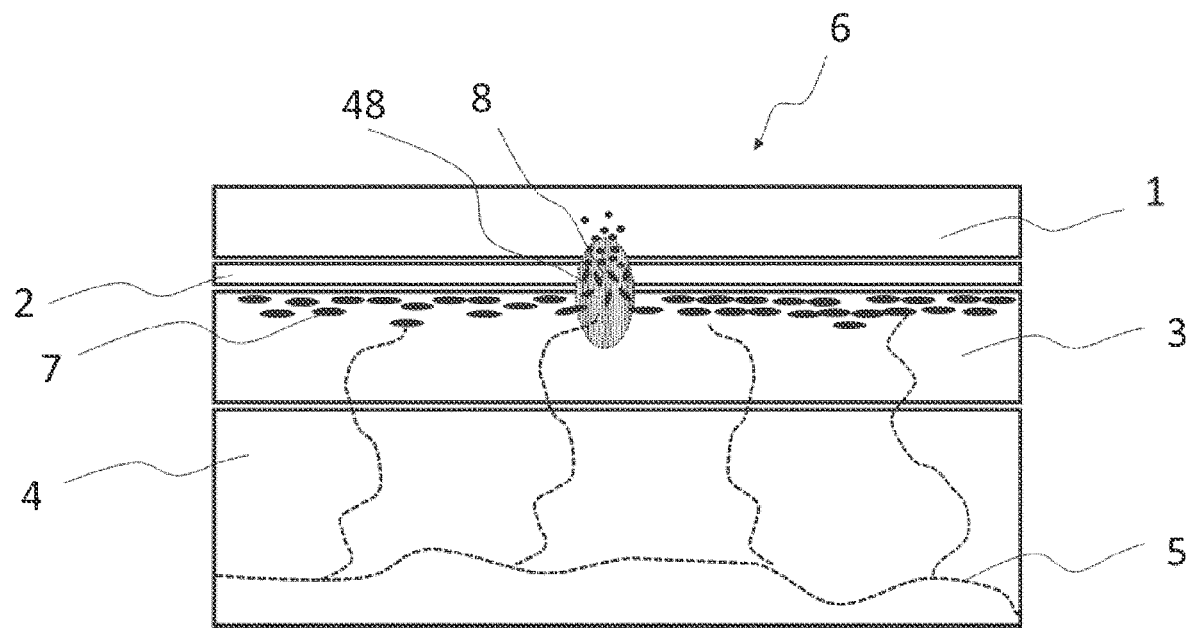
FIG. 4 illustrates a cross-section of the with a small lesion at the PoT located in the interface between dermis and epidermis, thus making a puncture in the basement membrane.

As illustrated in FIG. 4, the lesion will allow tattoo pigment 7 and dead pigment-containing cells to be expelled directly to the epidermis layer 1 through the punctured basement membrane 2. The epidermis layer 1 is subsequently renewed by the human body's normal renewal process, whereby the expelled pigment and dead pigment-containing cells are removed permanently.

Figure 5:
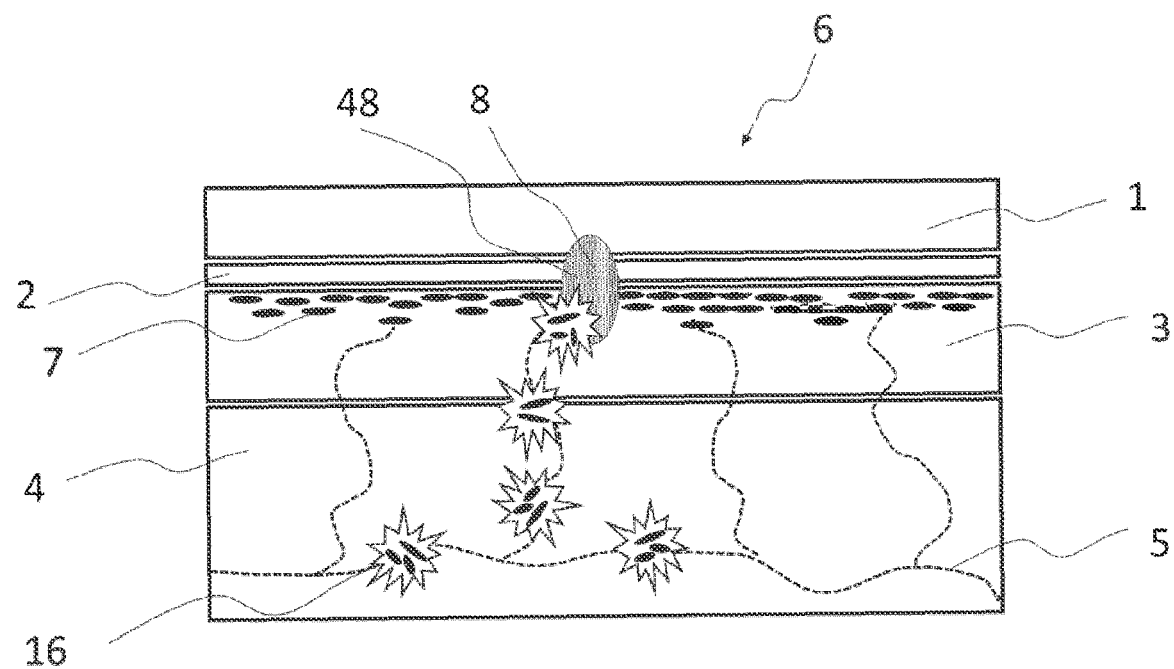
FIG. 5 illustrates a cross-section of skin with an immune-reaction initiated by the lesion at the PoT.

In addition to expelling pigment 7 via the body's natural renewal process, pigment may also be expelled via an immune reaction. FIG. 5 illustrates an immune reaction initiated by the lesion 48 at the PoT 8. During the immune reactions, active macrophages 16 will engulf foreign pigment particles 7 and dead pigment containing cells in the PoT 8 and transport them away from the dermis layer 3 through phagocytosis to the lymphatic system.

Figure 6:
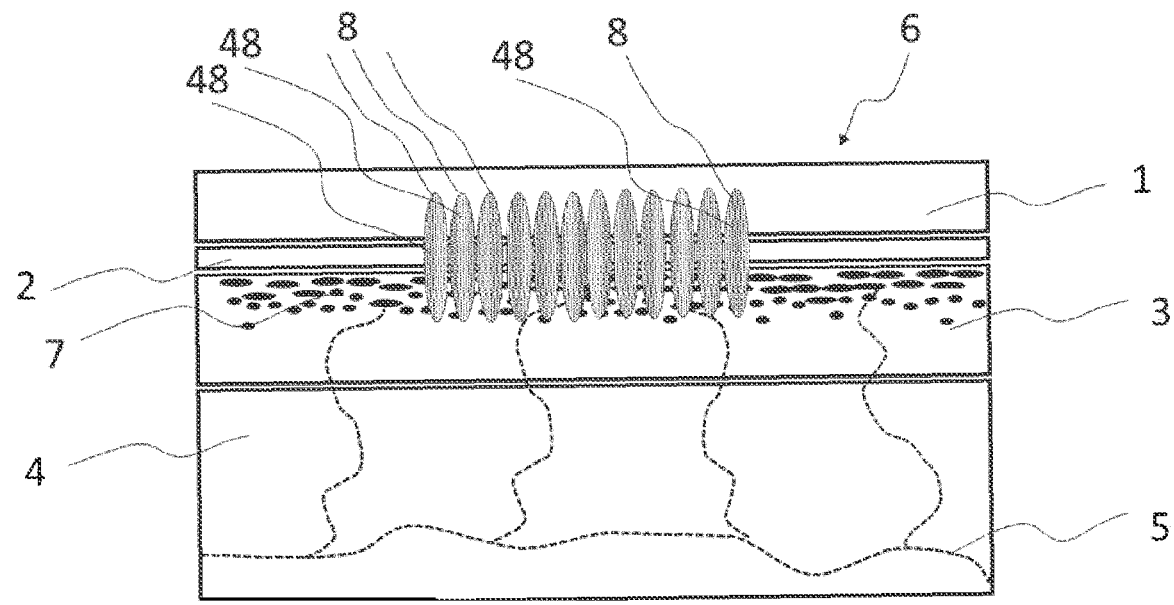
FIG. 6 illustrates a cross-section of skin with a plurality of lesions spaced to cover a volume in the interface between dermis and epidermis.

Although up to this point, we discussed a single PoT and its associated lesion, in preferred embodiments, a plurality of PoTs are used to form an equal number of lesions. FIG. 6, illustrates a series of lesions 48 positioned closely together in order to cover an area of the skin 6. The lesions will open the basement membrane 2, denaturate and coagulate the protein content in the dermis 3 and epidermis 1, and thereby decrease the internal adhesion between cells in the dermis and epidermis around the boundary of the PoT 8. In preferred embodiments, a plurality of PoTs are used to form multiple lesions. The lesions may be spaced any distance apart and created in any pattern. Various treatment methods including the number and spacing of PoTs and lesion will be discussed in more detail later in this document.

Figure 7:
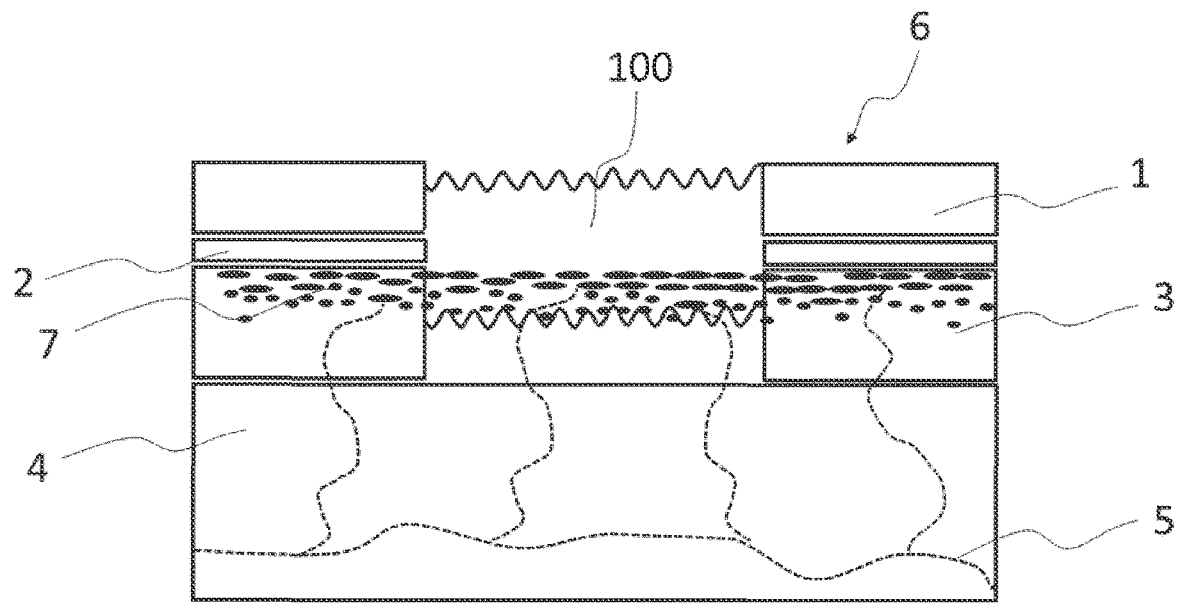
FIG. 7 illustrates a cross-section of skin where the treated volume within the PoTs and between the dermis and epidermis is no longer fully connected and nourished by the deeper layers of the dermis.
Figure 8:
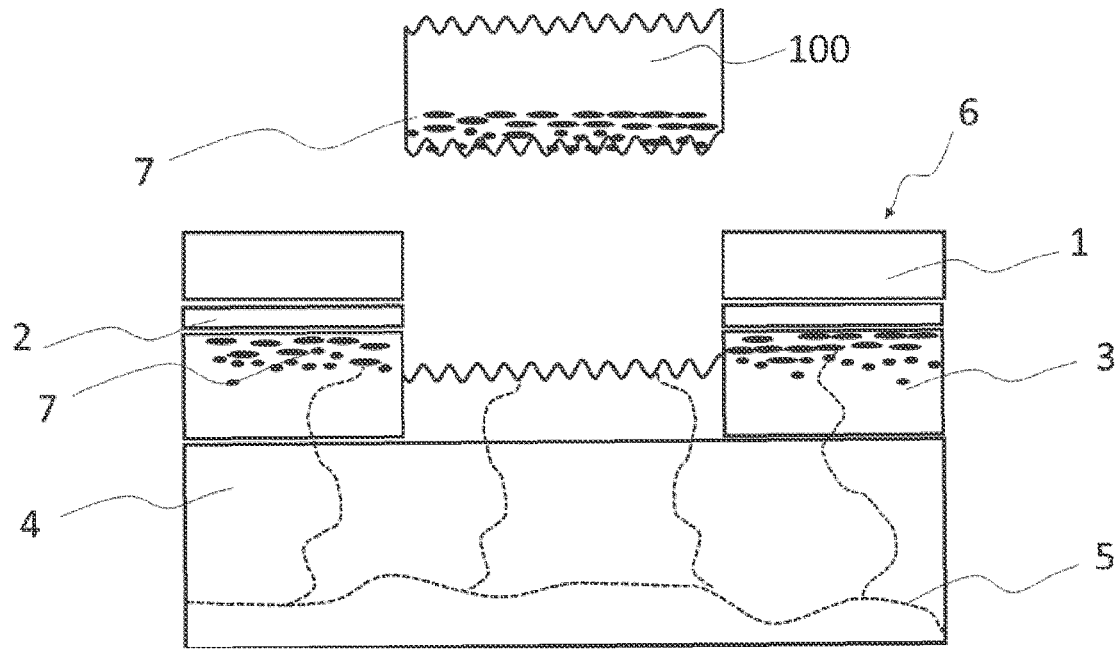
FIG. 8 illustrates a cross-section of skin with the separation and excretion of the treated volume of dermis and epidermis from FIG. 6.
Figure 9:
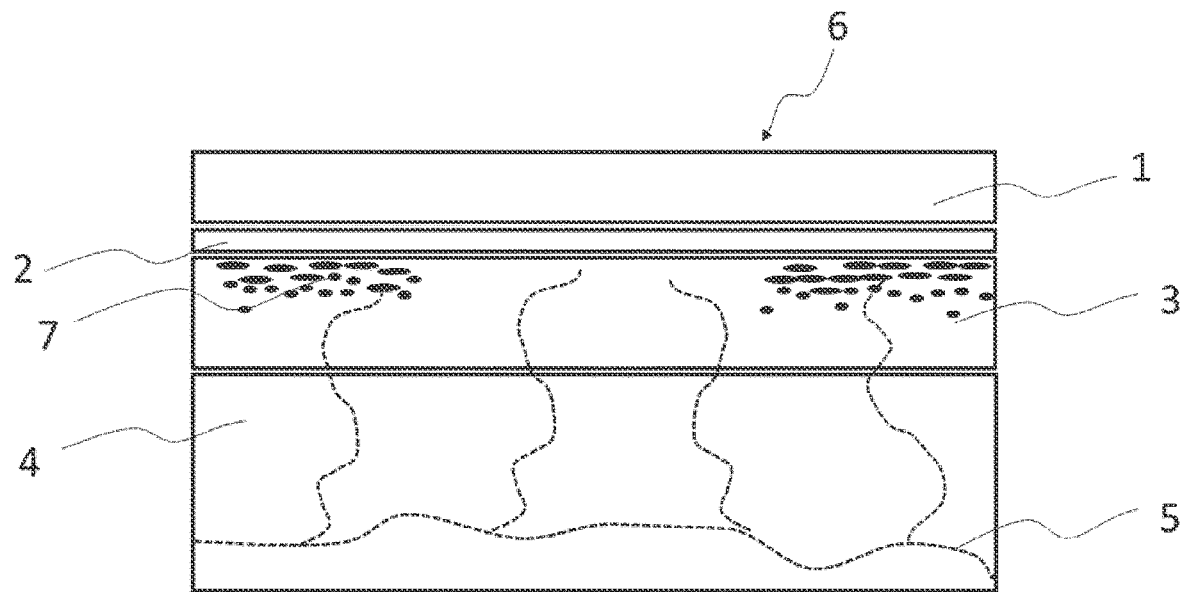
FIG. 9 illustrates a cross-section of skin following the treatment illustrated in FIG. 6 and after the body's healing process has completed and the excreted portion of the dermis and epidermis have closed.

The plurality of closely spaced lesions creates a volume of isolated cells 100 as illustrated in FIG. 7. As may be seen in FIG. 7, the lesions create a separation within the dermis and epidermis, where the treated volume within the PoTs and between the dermis and epidermis is no longer fully connected and nourished by the deeper layers of the dermis. After some time, the body will excrete the isolated and disconnected cells 100 as illustrated in FIG. 8. The normal healing process will subsequently replace excreted cells in the dermis 3 and epidermis 2 with new cells without pigments as illustrated in FIG. 9.

In addition to the excretion and replacement of cells that include pigment particles 7, pigment particles 7 that have agglomerated in the dermis layer 3 may also be scattered into smaller particles and subsequently transported away by one of the three methods mentioned above.

Focused Transducer

Figure 10:
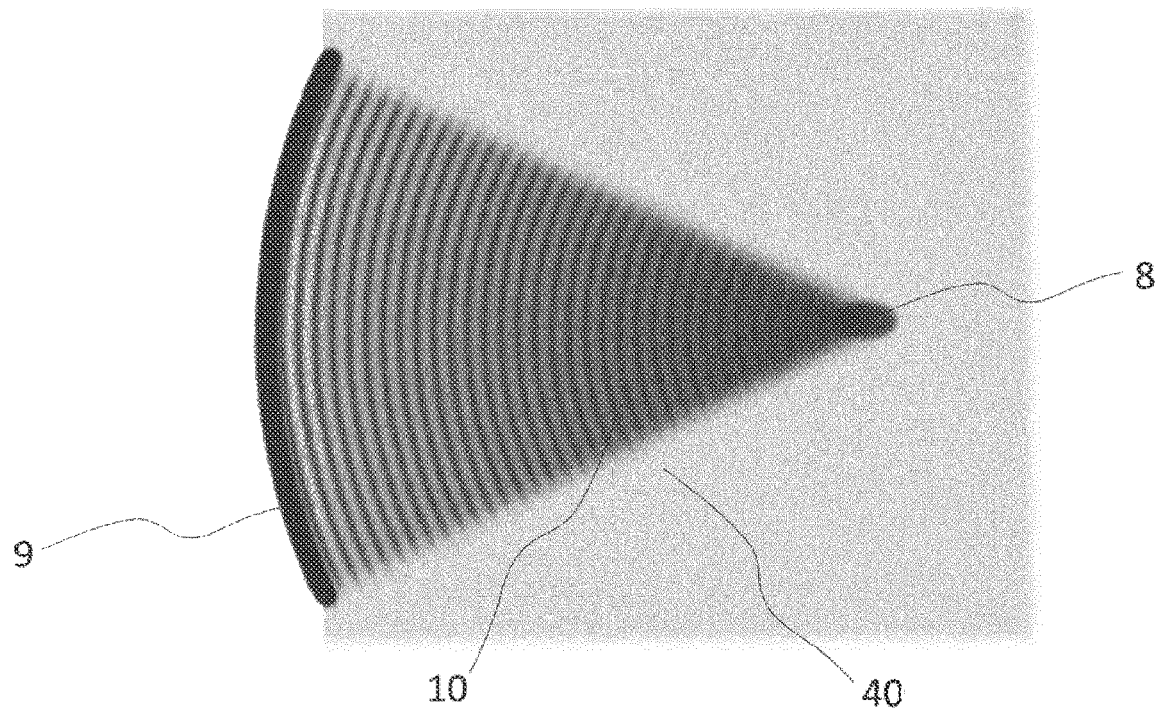
FIG. 10 illustrates a planar view of ultrasonic waves emitted by a focused transducer, which are concentrated into a small Point of Treatment (PoT).
Figure 11:
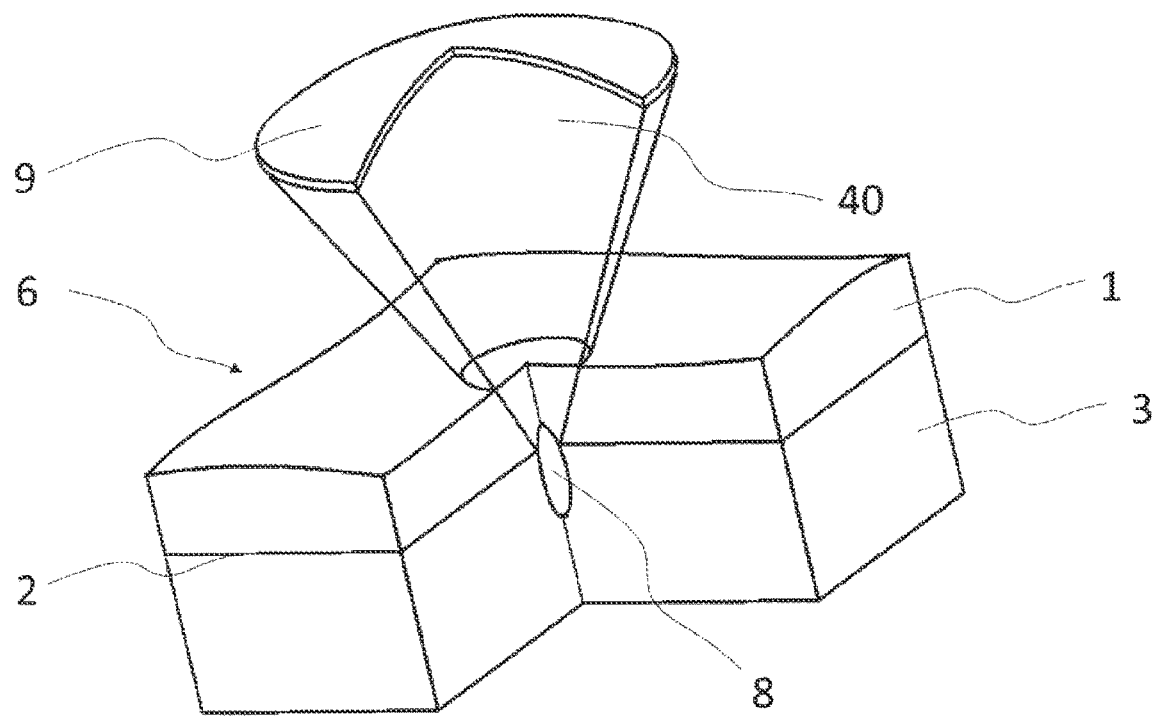
FIG. 11 illustrates a three-dimensional section of a focused ultrasonic transducer emitting acoustic waves, which are concentrated into a small Point of Treatment (PoT) in selected layers of skin.

FIG. 10 illustrates a planar view of ultrasonic waves 10 emitted by an acoustic generating device 9. The ultrasonic waves 10 are concentrated into a small PoT 8. A lesion 48 in a predefined PoT 8 is created by emitting an ultrasonic wave 10 through the coupling medium 40 and into a concentrated focal point as shown in FIG. 10 and FIG. 11. In preferred embodiments, the acoustic generating device 9 is made from piezoelectric material that generates the ultrasonic wave 10. Generally, the acoustic generating device 9 is connected to an electrical matching circuit 13 and housed in a dedicated housing 12, referred to in combination as a transducer 11, as shown in FIG. 12.

Figure 12:
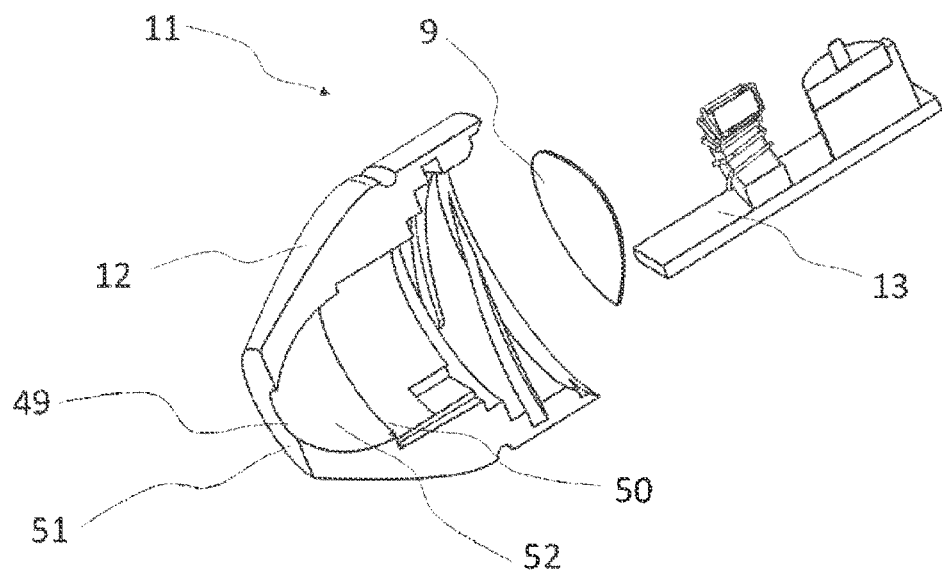
FIG. 12 illustrates an exploded three-dimensional isometric section view of a transducer that may be used for skin treatment.

FIG. 12 illustrates an exploded three-dimensional isometric section view of a transducer 11 that may be used for skin treatment. As may be seen in FIG. 12, the housing 12 includes a bevelled lip, edge or flange 50 to retain the acoustic generating device 9 and maintain a fixed distance from the acoustic generating device 9 and the end of the housing 51 designed to contact the skin. In some embodiments, the housing 50 has a window 49 in the end of the housing 51 designed to contact the skin. The window 49 may be generally smaller than the aperture of the acoustic generating device 9 because the acoustic waves will be focused. In the embodiment shown in FIG. 12, the window 49 is just a hole in the end of the housing 51. However, in other embodiments, the housing 12 may have a window 49 comprised from a transparent material integrated into the head 12.

In preferred embodiments, the housing 12 further has a cavity 52 between the acoustic generating device 9 and the end of the housing 51. As will be explained in more detail later, the cavity 52 is preferably filled with a coupling medium 40 to facilitate the transport of the acoustic waves from the acoustic generating device 9 to the end of the housing 51.

In preferred embodiments, the transducer 11 comprises an acoustic generating device 9 that is comprised of a piezoelectric element that has been fabricated into a section of a spherical shell with a specific geometrical focal length, an element thickness defining its thickness resonance frequency and a diameter defining its aperture. In one embodiment, the focal length is in the range from 5 to 30 mm, and thickness of the element ranges from 0.1 mm to 2 mm, while the aperture is in the range from 4 mm to 40 mm. In another embodiment, the focal length is in the range from 2 mm to 15 mm and thickness of the element ranges from 0.05 mm to 1 mm, while the aperture is in the range from 4 mm to 20 mm.

In yet another embodiment, the focal length is in the range from 10 mm to 200 mm and thickness of the piezoelectric element ranges from 0.1 mm to 2 mm, while the aperture is in the range from 20 mm to 100 mm. In this geometrical configuration, the acoustic generating piezoelectric element 9 can transform an electrical signal into an acoustic wave 10 with a defined focal point. The acoustic wave 10 generated by the piezoelectric element 9 is coupled to the surface on the end of the housing 51 of the transducer 11 using a coupling medium 40. An example of a and acoustic transducer element is given in Example 1.

Example 1

An acoustic transducer for skin treatment is comprising the following piezoelectric component:

| Material | MIL-STD-1376B Type 1 (PZT4) |
|---|---|
| Geometry | Circular focusing bowl |
| Outer diameter | 20 mm |
| Radius of curvature | 15 mm |
| Center hole diameter | 5 mm |
| Thickness | 0.2 to 0.3 mm |
| Fundamental thickness resonance | 5 to 10 MHz |
| 3$^{rd}$ Harmonic thick. resonance | 15 to 30 MHz |
| Electrode | Silver or other conductive material |

In some embodiments, the coupling medium 40 is a low loss medium capable of conducting acoustic waves from the focused transducer 9 to the surface of the skin above the PoT 8. The coupling medium preferably matches the acoustic impedance of the skin tissue, therefore in preferred embodiments, water is used as a coupling medium 40.

In another embodiment the low loss medium 40 consists of an acoustic coupling medium, which can be chosen from at least the following group: water-like media, acoustic coupling gels, aqueous polyacrylamide, hydrogels, methylmethacrylates, blends of collagen/poly (acrylic acid), poly vinyl alcohol and the like.

Acoustic Window

Figure 13:
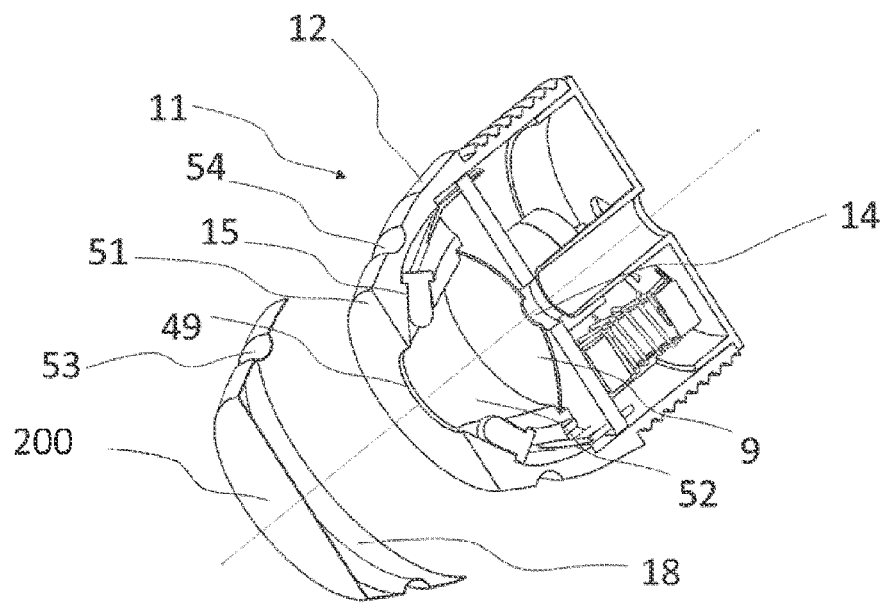
FIG. 13 illustrates an exploded three-dimensional isometric section view of a transducer head with an acoustic window used to provide acoustic coupling and physical protection during treatment of the skin.

FIG. 13 illustrates an exploded three-dimensional isometric section view of a transducer head 11 with an acoustic window 200. The acoustic window 200 may provide acoustic coupling and physical protection during treatment of the skin. As already explained above, a coupling medium 40 is desirably placed in the cavity 52 between the acoustic generating device 9 and the end of the housing 51. The coupling medium 40 is preferably retained in the cavity 52 and in embodiments where the end of the housing 51 includes a hole 49, a further acoustic window 200 may be used to cover the hole 49 and retain the coupling medium 49 in the cavity 52. In the embodiment shown in FIG. 3, the acoustic window is integrated as part of an acoustic coupler 18.

The acoustic coupler 18 may be permanently affixed to the housing 11 or as shown in FIG. 13, and more preferably, may be releasably coupled to the housing 12. In the embodiment shown in FIG. 13, the acoustic coupler 18 includes a protrusion or ridge 53 that runs around the inside perimeter. The protrusion 53 is designed to be releasably coupled to the groove 54 that runs around the perimeter of the housing 12. Accordingly, with the right amount of force the acoustic coupler 18 can be snapped on or off of the housing 12. A releasably coupled acoustic coupler 18 may be advantageous for a number of reasons including sanitary reasons. For example, because the acoustic coupler 18 may come in contact with the patient's skin, it may be made disposable and changed with each patient. In other embodiments, the acoustic coupler 18 is not disposable per se and may be wrapped in a disposable wrap which is discarded after each use. In yet another embodiment, the acoustic coupler 18 is affixed using adhesive layer that allows for easy removal.

Because the acoustic coupler 18 retains the coupling medium 40 in the cavity 52, between the element 9 and the surface of the skin above the PoT 8, the acoustic coupler is preferably sealed to the housing 12 adequately to prevent leaking of the coupling medium 40.

In one embodiment the acoustic window 200 is designed to allow an imaging capability integrated with the therapy transducer to have an adequate imaging access to the surface of the skin above the PoT 8. The placement of the therapy transducer may thereby be guided by visual observation through acoustic window.

In one a preferred embodiment the acoustic window 200 is made from a thin acoustically and optically transparent material like acrylic polymers, polyethylene, polyurethanes polycarbonates, polypropylene, polymethyl methacrylate, polysulfones, polystyrenes, styrene-butadiene copolymers, celluloses, thermoplastic polyesters, glass, sapphire, other types of crystal, silicone and the like. In other embodiments the acoustic window 200 can be made from non-optically transparent materials such as silicone rubber, latex, polyurethanes, polyesters, epoxies (with various fillings), polyamides, PTFEs, and the like.

In a preferred embodiment the acoustic window is composed of a 1-1000 μm thick film fabricated from optically and acoustically transparent polyethylene, polyurethanes or blends of polyurethanes and polyester elastomers.

Piezoelectric Element.

In a preferred embodiment, the acoustic generating device 9 may be a piezoelectric element. The piezoelectric element 9 may be made from a piezoelectric material such as doped lead zirconate titanate (PZT). PZT is a preferred choice because it has good energy conversion properties (high coupling coefficient $k_{33}$ and high value of $d_{33}$) and a relatively low cost.

In other embodiments the element 9 is made from alternative piezoelectric materials such as, but not limited to, single crystals made from lithium niobate (LNb), aluminium nitride (AlN), lead magnesium niobate-lead titanate (PMN-PT) or quartz; polycrystal ceramic materials made from lead-meta-niobate, potassium sodium niobate (KNN), barium titanate (BaT), bismuth titanate (BT), bismuth sodium titatanate (BNT), bismuth sodium titatanate-bismuth titanate (BNT-BT); or polymeric materials made from polyvinylidene fluoride (PVDF).

In other embodiments the acoustic generating device 9 can be replaced by an alternative active element, such as capacitive micromachined ultrasonic transducers (CMUTs), piezoelectric micromachined ultrasonic transducers (PMUTs) or similar.

In other embodiments, other materials may be used for the acoustic generating device 9 including combinations of materials and layers. In yet other embodiments, piezoelectric composites may be used for the focussed transducer 9.

In some embodiments, where the acoustic generating device 9 is a piezoelectric element, the device has a mechanical quality factor ($Q_m$) higher than 1000. In other embodiments, a $Q_m$ higher than 100 may be used.

In some embodiments, the acoustic generating device 9 is a planar element with an attached additional element (acoustic lens) used to focus the acoustic signal into a defined focal point. In some configurations, the lens is made from a low acoustic loss material characterised by the speed of sound that is lower than the speed of sound in medium 40 (e.g. water). In this case the lens is of convex shape, typically made from a polymer, for example PDMS (Poly-dimethylsiloxane), having typically 950 m/s speed of sound. In another configuration, the acoustic lens is of concave shape, being characterised by speed of sound that is higher than speed of sound in the medium 40. This can be achieved by employing composite materials, such as polymer filled with metallic filler. In one embodiment, the polymer is epoxy filled with Tungsten filler.

In yet other embodiments, the focusing of the ultrasonic wave 10 is obtained by other methods than described above, for example using electronic focusing techniques. In this configuration, the acoustic generating device 9 is comprised from multiple piezoelectric elements that are driven by a multi-output power driver. The focusing is obtained by the introduction of a specific delay between the driving signals so that the focused wave arrives at the PoT 8 in the pre-determined manner. In some embodiments, the multi-element transducer comprises more than 1 element. In another embodiment, the transducer comprises between 2 and 256 elements.

Figure 14:
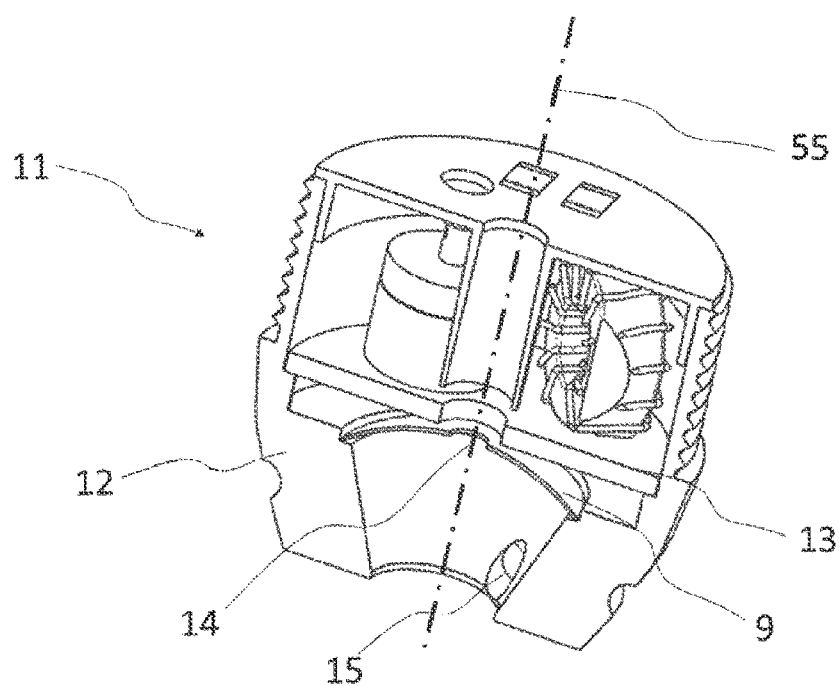
FIG. 14 illustrates an isometric three-dimensional section view of the Transducer as in FIG. 13.

FIG. 14 illustrates an isometric three-dimensional section view of the transducer 11 as shown in FIG. 13. As may be seen in FIG. 14, the acoustic generating device 9, regardless of whether it is constructed as a single focused piezoelectric element, a multielement component, or by a planar element with an attached element used to focus the acoustic signal, may be manufactured with a hole 14. In preferred embodiments, the hole 14 is in the center of the acoustic generating device 9 along the focusing axis or acoustic axis 55. As may be appreciated, in the embodiment shown in FIG. 14, the acoustic axis 55 is also the longitudinal axis of the device. The hole 14 allows for mechanical stress relive during high-power operation of the piezoelectric element 9. In addition, the hole 14 may be used to allow for optical access of an auxiliary imaging system.

Figure 15:
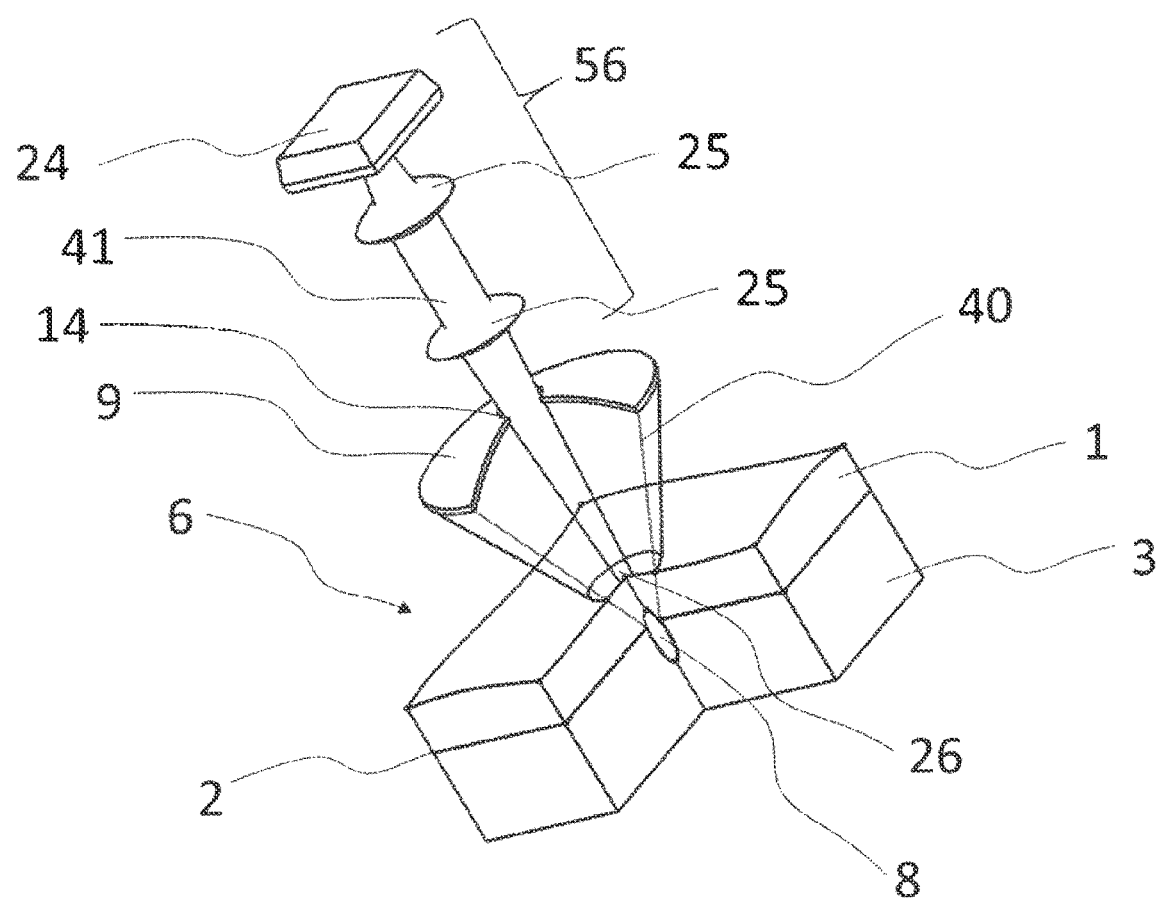
FIG. 15 illustrates a three-dimensional section view of a basic arrangement of the main internal components of a focused piezoelectric transducer with an optical monitoring system mounted with an optically transparent pathway through the piezoceramic element.

FIG. 15 illustrates a three-dimensional section view of a basic arrangement of the main internal components 24 and 25 of a focused piezoelectric transducer with an optical monitoring system 56 mounted with an optically transparent pathway 41 through the piezoceramic element 9. As may be appreciated, the optical monitoring system may include at least one lens 25. In some embodiments, the optical monitoring system may include a CCD 24 or other type of optical imaging device. In preferred embodiments, the optical axis of the optical monitoring system 56 is aligned with the acoustic axis 55 and creates a line of sight to the skin surface 6, as schematically illustrated FIG. 15.

In order to create an optically transparent pathway 41, the acoustic generating device 9 needs to have a hole 14. In one embodiment, the diameter of the hole 14 is in the range from 1 mm to 10 mm. In another embodiment, the diameter of the hole is in range from 0.2 mm to 20 mm. Preferably, the hole diameter is restrained by the aperture of the piezoelectric element, so the diameter of the optically transparent pathway 41 is not more than 50% of the aperture of the piezoelectric element. In other embodiments the diameter of the hole 14 is not more than 70% of the total diameter of the acoustic generating device 9.

Figure 16:
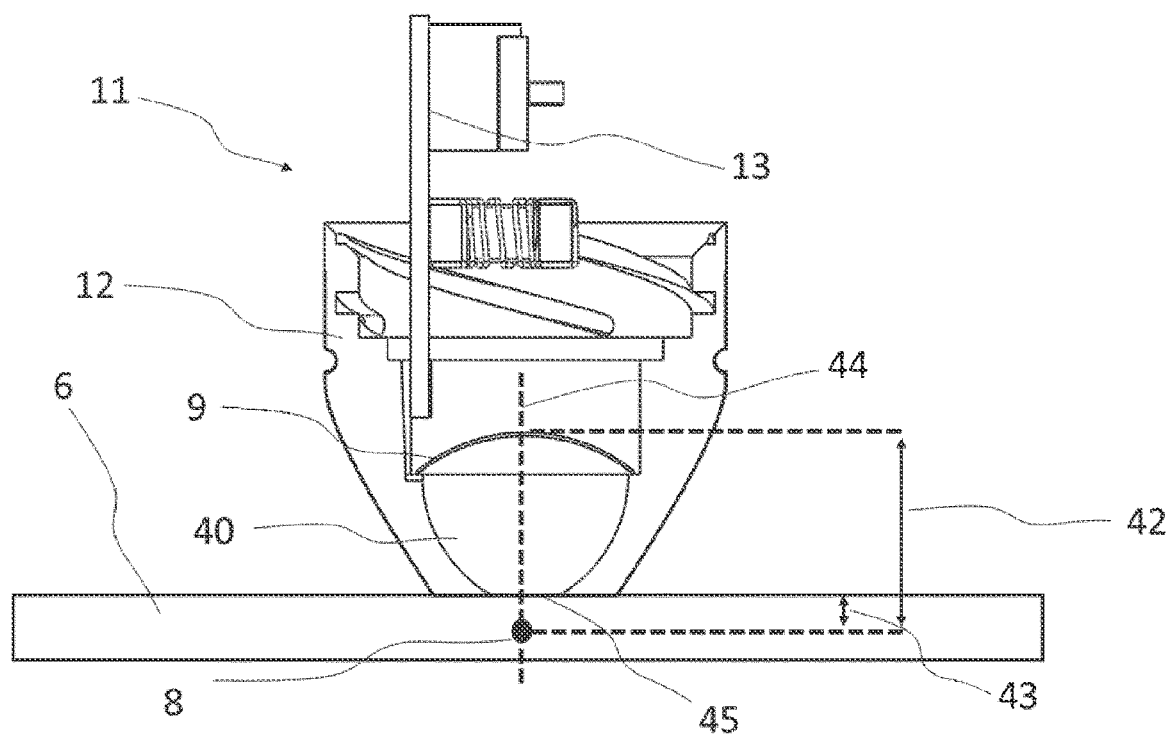
FIG. 16 depicts a planar section of the basic configuration of a transducer in contact with a skin surface.

FIG. 16 depicts a planar section of the basic configuration of a transducer head 11 in contact with a skin surface. In preferred embodiments, the transducer 11 comprises a piezoelectric element 9 characterised by its acoustical focal distance 42. The acoustic local distance 42 is larger than the distance from the surface of the piezoelectric element 9 along its axis 44 to the transducer front face 45, defining the transducer penetration depth 43. In this way, the PoT 8 is located in the dermis 3 and/or epidermis 1 layer and the lesion 48 will expand towards the surface of the skin through the basement membrane 2 and into the epidermis layer during the treatment. As shown, the transducer 12 front face 45 is in contact with the skin surface 6 during treatment as illustrated in FIG. 16 and FIG. 17.

As previously discussed, the volume inside the transducer housing 12 between the piezoelectric element 9 and the face touching the skin 45 may be filled with a coupling media 40. In such embodiments, the hole 14 may further include a transparent window to prevent the coupling media 40 from escaping through the hole 14 into the device 11. The window in hole 14 may be made from similar materials to other windows disclosed herein.

Figure 17:
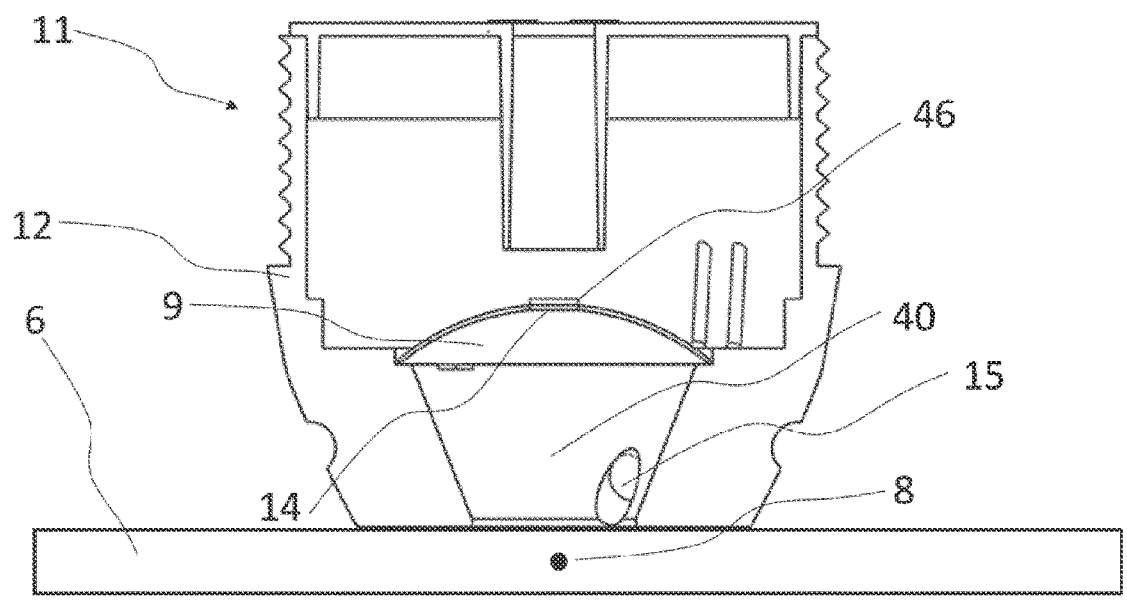
FIG. 17 depicts a planar section of the basic configuration of a transducer with optical monitoring capability in contact with skin surface.

FIG. 17 depicts a planar section of the basic configuration of a transducer 11 with optical monitoring capability in contact with skin surface. In preferred embodiments, the PoT 8 is positioned 0.1 mm to 10.0 mm below the surface of the skin, depending on skin type and the location of the treated area on the human body. The depth of the PoT 8 should be fixed to target a chosen depth from 0.1 mm to 10.0 mm into the dermis layer 3, where most of the pigment 7 and pigment-containing cells from tattoos are located (See FIG. 3). The location of the tattoo and the type of skin are both considerations in determining the correct depth below the surface of the skin for the PoT 8. In some embodiments, the penetration depth of any particular transducer head 11 is fixed and different transducer heads 11 with different acoustic penetration depths are employed depending on the part of the body the tattoo needs to be removed from. To this end, transducer heads 11 may be removeably coupled from a higher-level hand-held assembly. In other embodiments, electronic beam steering is used to electronically control the penetration depth on a single transducer head 11. In this configuration, one or more multi-element transducers may be used.

Wavelength and Resonances

The ability to determine and/or control the size of a lesion is an important part of the embodiments described herein. Assuming that a lesion shape can be approximated by an ellipsoid elongated along the axis perpendicular to the skin surface (Z-direction), the size of the lesion defined by its diameter in the X-Y-plane should in some embodiments not be bigger than 10.0 mm.

Figure 18:
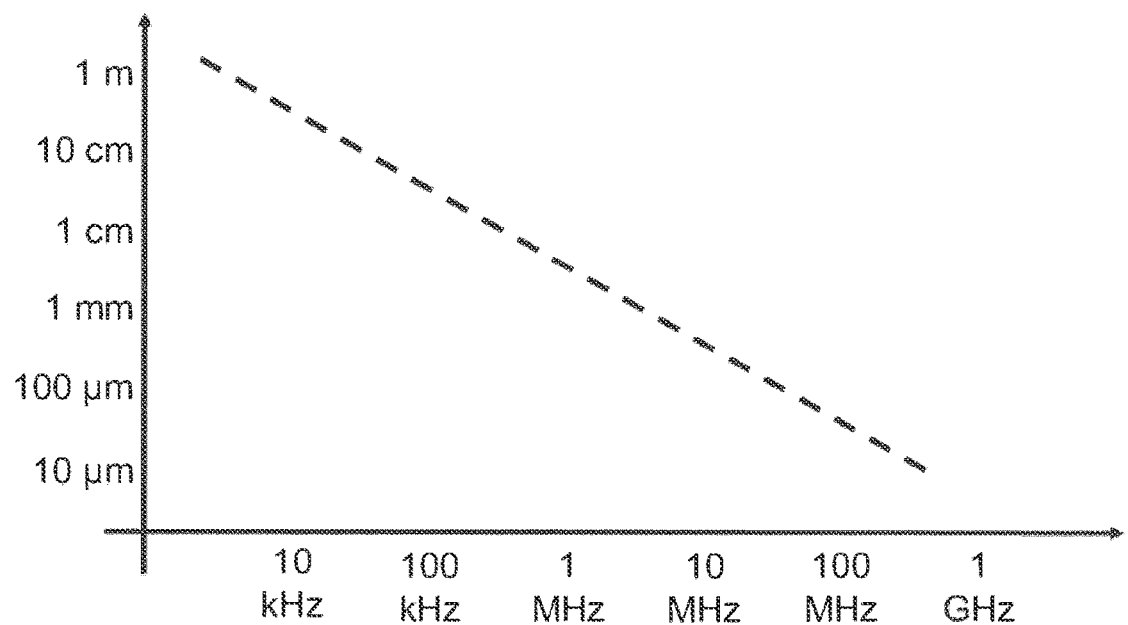
FIG. 18 is a graph that illustrates the relation between transmitted acoustic frequency and wavelength.

In preferred embodiments, the size of the lesion defined by its diameter are 2.0 mm or smaller. Considering the fact that resonance frequencies for creation of lesions below 1 mm are above 10 MHz, the corresponding ultrasonic wavelengths must be below 150 µm as illustrated in FIG. 18. This will in turn mean certain constraints on the dimensioning of the piezoelectric spherically focused element.

In preferred embodiments, the operating frequency of the system is 7 MHz or above. In a more preferable embodiment this frequency is 15 MHz or above. This patent application teaches how to achieve these higher frequencies of operation by designing the piezoelectric element using the relationships between wavelength, resonance frequencies, and element size.

Figure 19:
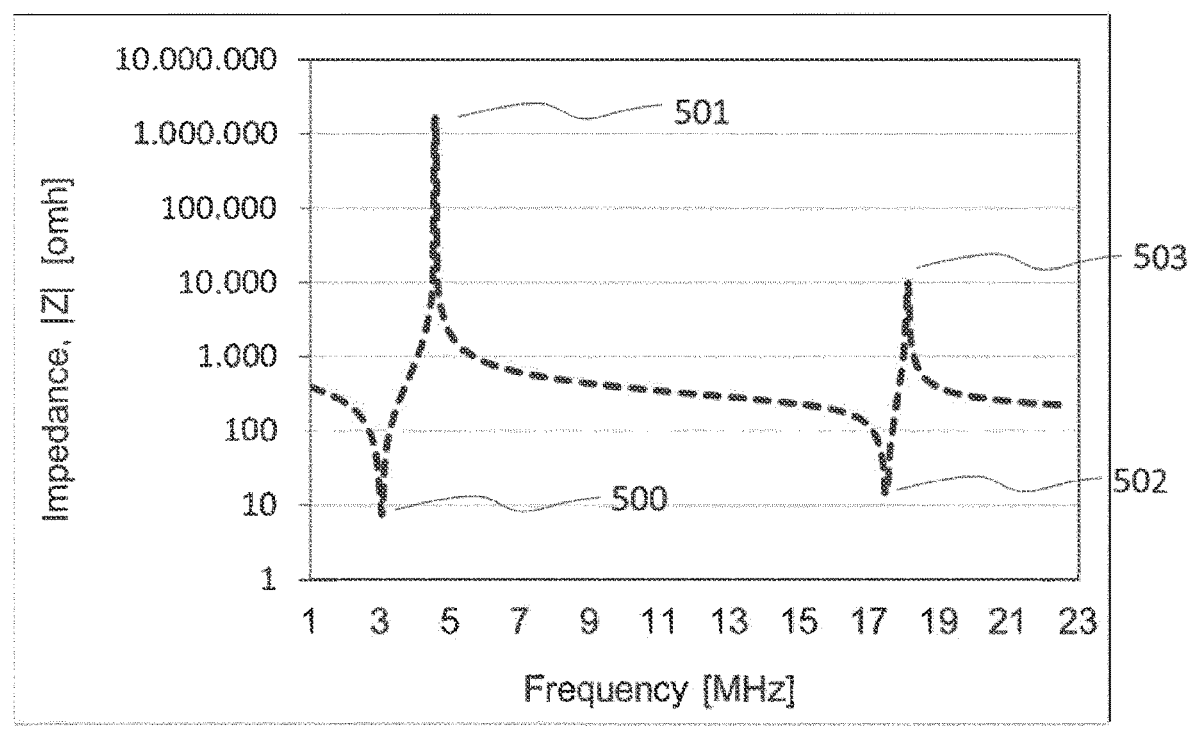
FIG. 19 is a graph that illustrates an example of an impedance plot of a piezoelectric element.

FIG. 19 is a graph that illustrates an example of an impedance plot of a piezoelectric element. As shown in FIG. 19, a piezoelectric element exhibits a particular thickness resonance mode corresponding to certain vibration phenomena. It manifests itself in specific impedance spectrum patterns as illustrated in FIG. 19. The fundamental thickness resonance frequency $f_1$ 500 of a piezoelectric element can be calculated from the following formula:

$$f_1 = \frac{c_p}{2h}$$

Where h is the thickness of the piezoelectric element and $c_p$ is the speed of sound in the piezoelectric material. Higher order resonance modes can also be found for the following conditions:

$$f_n = \alpha n f_1, \text{ for } n=3,5,7,9, \ldots.$$

Where a is a factor depending on the actual geometrical configuration of the piezoelectric element. For practical applications, a value of 1.1 can be used.

In preferred embodiments, the system is operating at frequencies higher than 15 MHz. In order to achieve frequencies above 15 MHz with a focused transducer 9 made from a piezoelectric element operating in its fundamental mode, the piezoelectric element would require a thickness below 0.1 mm as given in Example 2. Piezoelectric elements with a thickness below 0.1 mm are very difficult and/or costly to manufacture. Accordingly, in designing a focused transducer, more creative methods may be implemented.

In some embodiments, the fundamental resonance mode is used to drive the piezoelectric spherically focused element 9 at resonance frequencies between 1 MHz and 50 MHz. In preferred embodiments, the third harmonic resonance mode 502 is used to drive the piezoelectric element at a resonance frequency between 1 and 50 MHz. It may also be appreciated that other harmonic resonance modes may be used including the second and fourth harmonic modes. In yet other embodiments, higher order resonance modes, such as the $5^{th}$, $7^{th}$, $9^{th}$ etc., are used to drive the piezoelectric element at resonance frequencies between 10 and 100 MHz.

Example 2

A piezoelectric spherically focused element is required to operate at a fundamental thickness resonance frequency $f_1$ of 20 MHz. The necessary wall thickness, h, can thus be calculated assuming sound velocity in piezoelectric element equal to $c_p$=4000 m/s as follows:

$$h = \frac{c_p}{2f_1} = 0.1 \text{mm}$$

Example 3

A piezoelectric spherically focused element as in Example 2 is required to operate at a thickness $3^{rd}$ harmonic of resonance frequency $f_3$ around 20 MHz. The necessary wall thickness, h, can thus be calculated from the following formulas:

$$f_1 = \frac{f_3}{3\alpha} = 6.1 \text{MHz}$$

$$h = \frac{c_p}{2f_1} = 0.33 \text{mm}$$

TABLE 1

| Resonance frequency [MHz] | Element thickness using fundamental resonance [µm] | Element thickness using third harmonic resonance [µm] |
|---|---|---|
| 5 | 400 | 1320 |
| 10 | 200 | 660 |
| 15 | 133 | 440 |
| 20 | 100 | 330 |
| 25 | 80 | 264 |
| 30 | 67 | 220 |
| 40 | 50 | 165 |
| 50 | 40 | 132 |
| 100 | 20 | 66 |

The piezoelectric elements are typically machined from brittle piezoceramics in order to achieve the required thickness and shape. At thicknesses below 200 µm, piezoceramics are inherently very difficult to handle and difficult to machine due to their low mechanical integrity. Hence, it is advantageous to use a third harmonic resonance as thickness of an element is approximately three times larger compared to an element working at a fundamental frequency. This is especially true for the frequency range above 10 MHz.

Given the relatively small dimensional features of the skin, a small and well-controlled lesion is required in the PoT. The concentration and focusing of the ultrasound waves therefore need to be controlled as precisely as possible.

Figure 20:
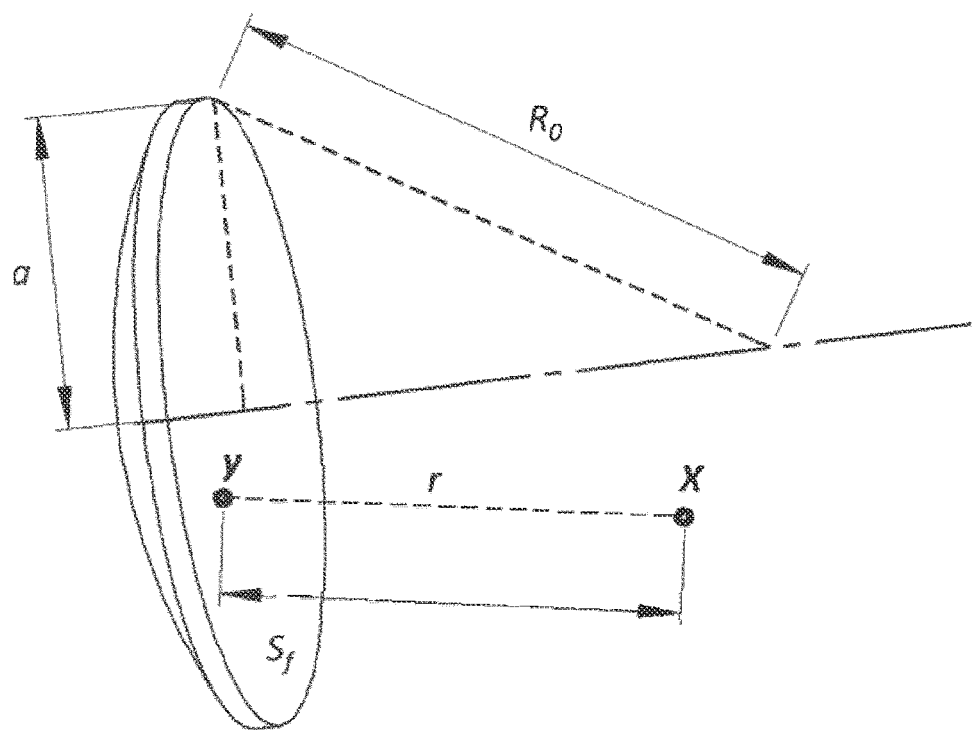
FIG. 20 is a three-dimensional isometric view of the focused piston arrangement of a spherical transducer.
Figure 21:
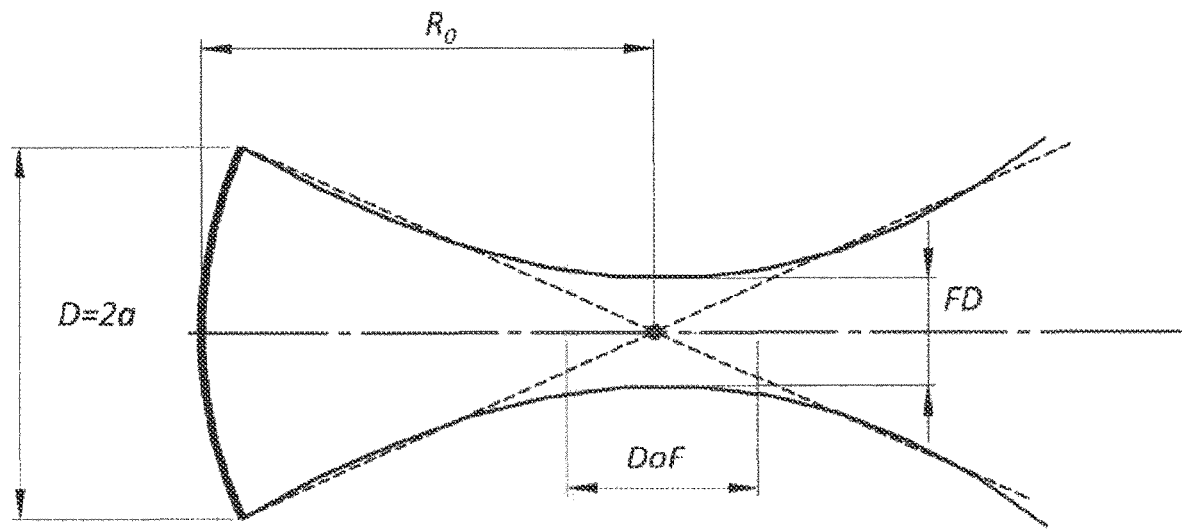
FIG. 21 illustrates the schematic shape of a pressure field created by a focused piston like the one shown in FIG. 20.

The ultrasound pressure field produced by piezoelectric focused element can be well modelled by a focused cylinder according to O'Neil model (O'Neil H. T. Theory of focusing radiators, J. Acoust. Soc. Am., 21, 616-526, 1949). One can consider a structure depicted in FIG. 20, where a rigid surface $S_f$ of a focused piston of an aperture a and radius of curvature $R_0$ is vibrating with vibration velocity $v_0$ and angular frequency $\omega=2\pi f$ into the fluid of density $\rho$ and sound velocity c. Then the pressure $p(x,\omega)$ in front of the piston in the arbitrary point in space x can be described as follows:

$$p(x, \omega) = \frac{-\omega \rho v_0}{2\pi} \int_{S_f} \frac{\exp(ikr)}{r} dS(y) \quad \text{(Eq. 1)}$$

where y are coordinates of the radiating point on the surface of the focused piston, r is the distance between y and point of interest x, k is the wave number $$k = \frac{2\pi}{\lambda}, \text{ while } \lambda = \frac{c}{f}$$

being the wavelength. Given that the condition $$R_0 << \frac{D^2}{2\lambda}$$

is met, one can assume that an efficient focusing occurs and the pressure field can be schematically depicted as in FIG. 21.

Figure 22:
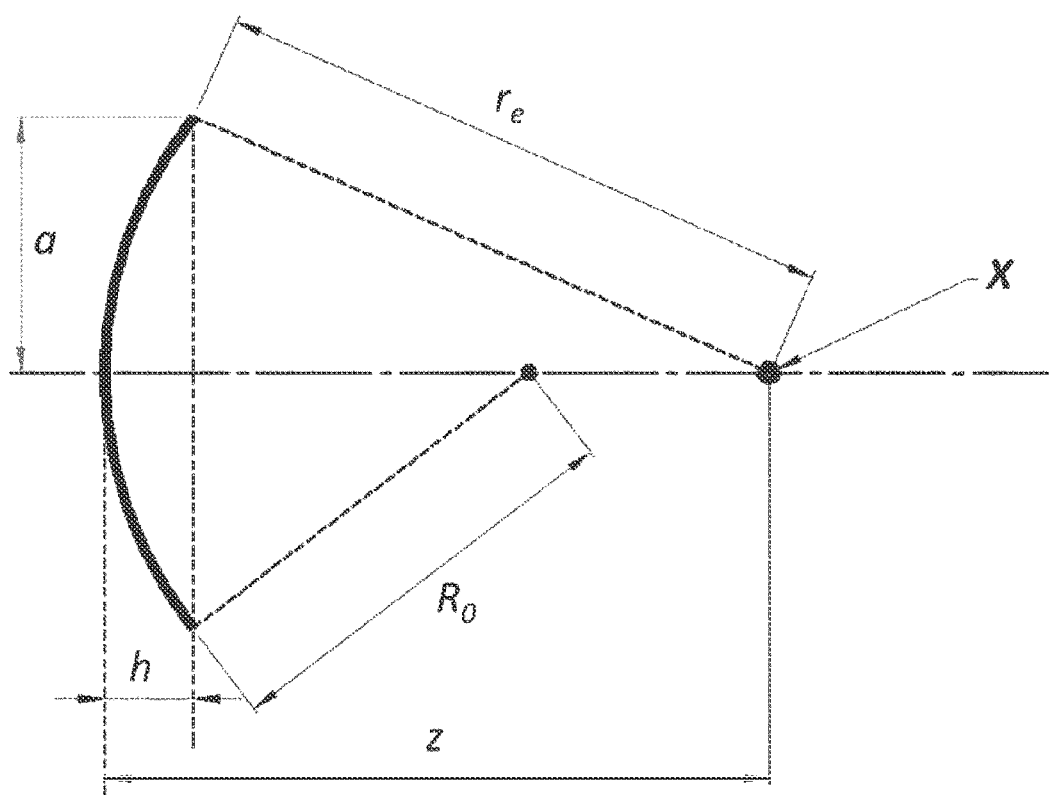
FIG. 22 illustrates a cross-sectional schematic of the focussing element of a focussed transducer for the purpose of illustrating the derivation of the pressure profile along the centre axis.

It is very useful to evaluate the pressure profile along the central axis of the focused piston as depicted in FIG. 22. For a given point x along the central axis the pressure derived from Eq. 1 is given by $$p(x, \omega) = \frac{\rho c v_0}{q_0} [\exp(ikz) - \exp(ikr_e)] \quad \text{(Eq. 2)}$$

where $$q_0 = 1 - \frac{z}{R_0}, r_e = \sqrt{(z-h)^2 - a^2}, h = R_0 - \sqrt{R_0 - a^2}.$$

Figure 23:
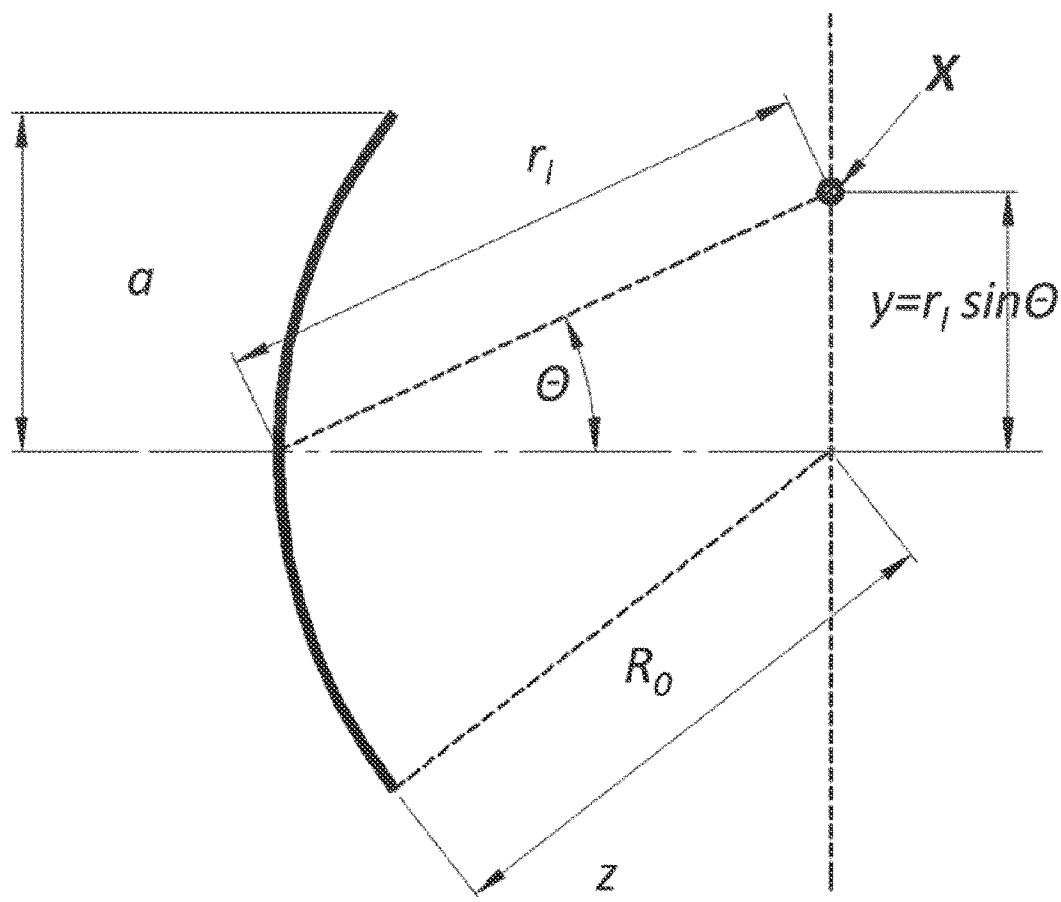
FIG. 23 illustrates a cross-sectional schematic of the focussing element of a focussed transducer for the purpose of arrangements and symbols used to derive the pressure profile in the focal plane.

Another important pressure profile is located in the plane at the vicinity of the geometric focus as illustrated in FIG. 23. For a given point x along the line perpendicular to the central axis and coinciding with the geometric focus the pressure is expressed by the following derived from Eq. 1

$$p(x, \omega) = -i\omega \rho c v_0 a^2 \frac{\exp(ikr_l)}{r_l} \frac{J_1(kay/r_l)}{kay/r_l} \quad \text{(Eq. 3)}$$

where $J_1(x)$ is a first order Bessel function of the first kind.

It is useful to define F-number of the radiator as $$FN = \frac{R_0}{2a}.$$

Example 4

Figure 24:
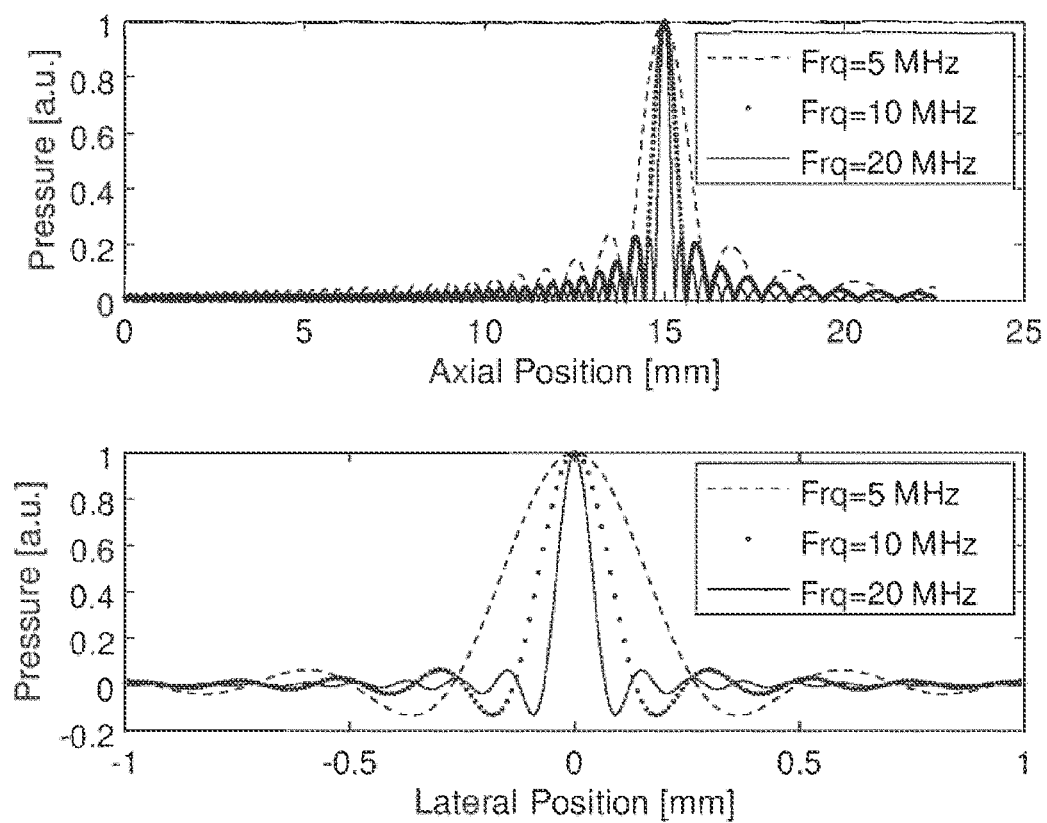
FIG. 24 is a graph that depicts the pressure profiles along the central and lateral axes at 5, 10 and 20 MHz for a given configuration of a focused piston.

A focused radiator of the aperture equal to 10 mm and radius of curvature equal to 15 mm is driven by three different frequencies 5 MHz, 10 MHz, 20 MHz. The radiator is radiating acoustic energy into water at the speed of sound equal to 1480 m/s and density 1000 kg/m³. The pressure profiles along central axis as well as in the focal plane calculated according to Eq. 2 and Eq. 3 are given in FIG. 24. One can appreciate the impact of frequency on the size of the pressure peak in the vicinity of the focus.

Example 5

Figure 25:
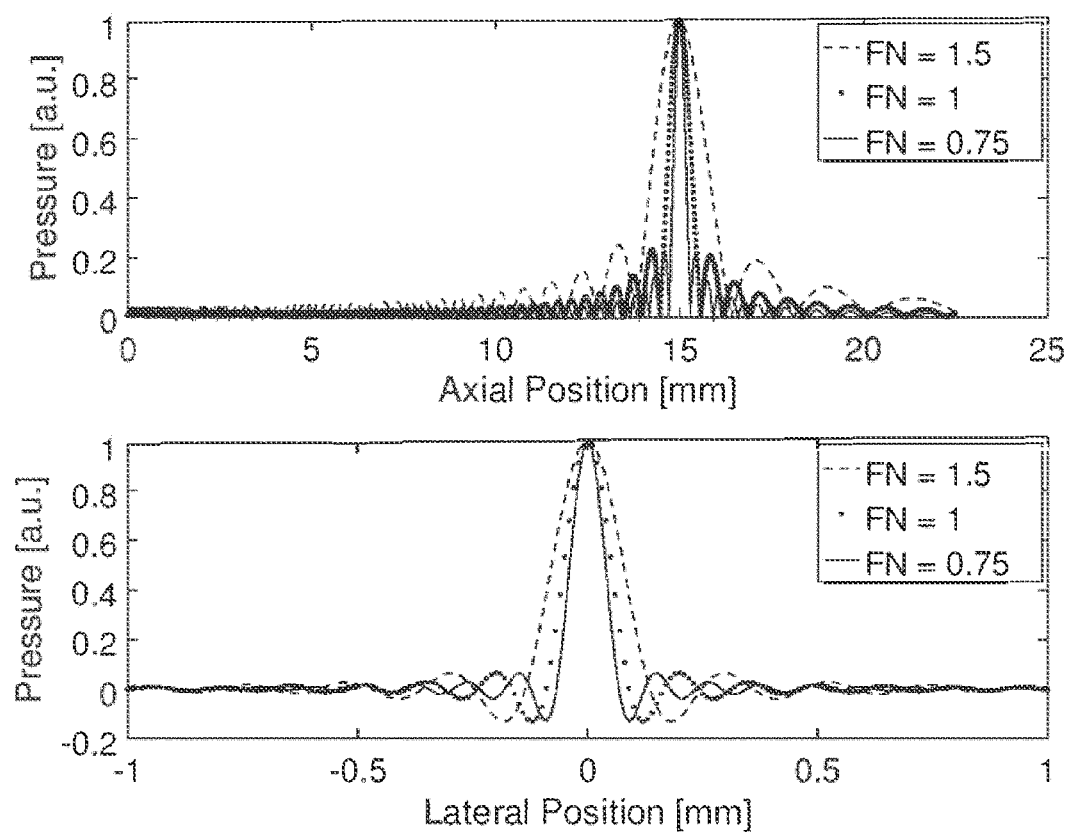
FIG. 25 is a graph that depicts the pressure profiles along the central and lateral axes at three different apertures for a given configuration of a focused piston.

A focused radiator of three different apertures equal to 10 mm (FN=0.75), 7.5 mm (FN=1) and 5 mm (FN=1.5) and radius of curvature equal to 15 mm is driven at frequency equal to 20 MHz. The radiator is radiating acoustic energy into water at the speed of sound equal to 1480 m/s and density 1000 kg/m³. The pressure profiles along central axis as well as in the focal plane calculated according to Eq. 2 and Eq. 3 are given in FIG. 25. One can appreciate the impact of aperture size at constant radius of curvature on the size of the pressure peak in the vicinity of the focus, where lower F—number radiators are more preferable for creation of small and highly focused pressure peaks.

Example 6

Figure 26:
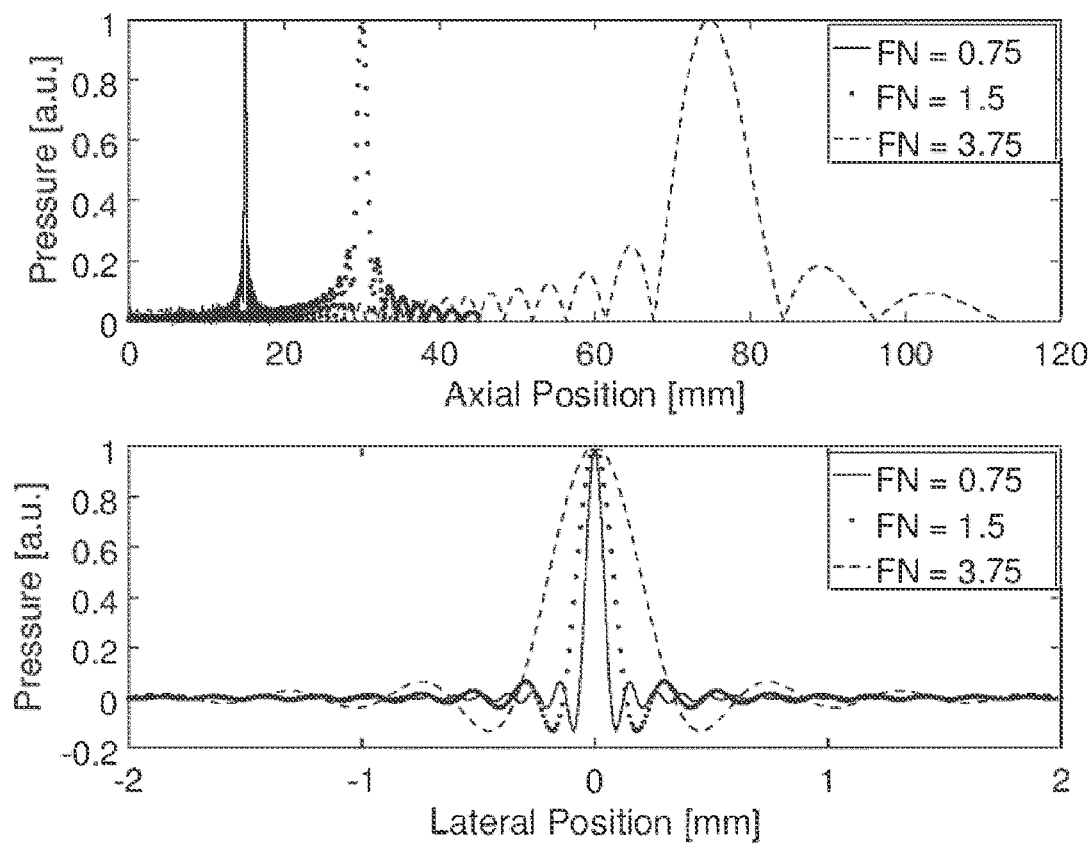
FIG. 26 is a graph that depicts the pressure profiles along the central and lateral axes at three different radii of curvature for a given configuration of a focused piston.

A focused radiator of three different radii of curvature equal to 15 mm (FN=0.75), 30 mm (FN=1.5) and 75 mm (FN=3.5) and aperture equal to 10 mm is driven at frequency equal to 20 MHz. The radiator is radiating acoustic energy into water at the speed of sound equal to 1480 m/s and density 1000 kg/m³. The pressure profiles along central axis as well as in the focal plane calculated according to Eq. 2 and Eq. 3 are given in FIG. 26. One can appreciate the impact of radius of curvature on the size of the pressure peak in the vicinity of the focus, lower F—number radiators are more preferable for creation of small and highly focused pressure peaks.

One can use equations Eq. 2 and Eq. 3 to evaluate the size of the focal zone defined as the volume in which the pressure drops by 6 dB in relation to the peak value. As depicted in FIG. 21 the distance along central axis over which pressure drops by 6 dB is called depth of focus (DoF), and similarly, this distance along the focal plane is called focal diameter (FD).

One can derive from Eq. 3 that the focal diameter FD of a focused ultrasonic can be approximated by:

$$FD(6dB) \approx 1.44\left(\frac{R_0}{2a}\right)\lambda = 1.44 FN\lambda,$$

where a is the aperture of the spherically focused transducer of radius of curvature $R_0$ and $\lambda$ is the wavelength of the soundwave emitted from the focused element of F-number FN.

Similarly, the depth of focus DoF of a piezoelectric spherically focused element can derived from Eq. 2 and be approximated by the following formula:

$$DoF(6dB) \approx 9.68\left(\frac{R_0}{2a}\right)^2 \lambda = 9.68 FN\lambda.$$

Example 7

A piezoelectric spherically focused element made from a hard PZT material (e.g. Navy type I) is operated in water (c—comparable to speed of sound in tissue) under the following conditions:

| Parameter | Symbol | Value | Unit |
| --- | --- | --- | --- |
| Sound velocity in water | c | 1480 | m/s |
| Frequency | f | 6.66 | MHz |
| Element diameter | D | 20 | mm |
| Element Focal radius | $R_0$ | 15 | mm |

Given the formulas mentioned above, one can calculate that the wavelength of acoustic wave in tissue (similar to water) would be 148 µm. This will result in a 6 dB focal zone, characterised by focal diameter of 240 µm with a depth of focus of 1210 µm.

Example 8

A piezoelectric spherically focused element made from a hard PZT material (e.g. Navy type I) is operated in water (c—comparable to speed of sound in tissue) under the same conditions as in Example 2, but at a $3^{rd}$ harmonic frequency of 20 MHz:

| Parameter | Symbol | Value | Unit |
| --- | --- | --- | --- |
| Sound velocity in water | c | 1480 | m/s |
| Frequency | f | 20.00 | MHz |
| Element diameter | D | 20 | mm |
| Element Focal radius | $R_0$ | 15 | mm |

Using the formulas mentioned above, one can calculate the wavelength of an acoustic wave in tissue (similar to water) would be 74 µm. This smaller wavelength, compared with that generated by a 6.66 MHz element, will result in a smaller 6 dB focal zone characterised by focal diameter of 80 µm and a depth of focus of 403 µm.

Small and well-defined lesions in the PoT 8 are desired. This means that the focal diameter of the lesion as well as the depth of focus is balanced to the dimensional constrains of the dermis- and epidermis-layers around the PoT. As shown in the above examples, this can be obtained by using a high resonance frequency for the piezoelectric spherically focused element.

In one embodiment, the frequency used to obtain a small and well-defined lesion in the PoT 8 at a resonance frequency 500 from 15 to 50 MHz is therefore used to drive the piezoelectric focused element.

In preferred embodiments, the frequency used to obtain a small and well-defined lesion in the PoT 8 at a resonance frequency from 7 to 50 MHz is used to drive the piezoelectric focused element working at $3^{rd}$ harmonic frequency in the parallel resonance 503.

In another preferred embodiment, the frequency used to obtain a small and well-defined lesion in the PoT 8 at a resonance frequency from 15 to 100 MHz is used to drive the piezoelectric focused element working at $5^{th}$ or higher odd harmonic frequency in the parallel resonance.

For other embodiments, the range of resonance frequencies used to drive the piezoelectric focused element can be from 5 to 15 MHz to obtain larger thermal lesions in areas of the body where the dermis-layer is relatively thick.

For yet other embodiments, the range of resonance frequencies used to drive the piezoelectric focused element can be from 20 to 50 MHz to obtain very small thermal lesions in areas of the body where the dermis-layer is thin.

Impedance Matching

Efficiency of power and energy transfer between the energy source and the transducer is determined by the electrical impedance of the source (e.g. RF power amplifier) and the input impedance of the transducer. The optimal energy transfer is obtained when the complex output impedance of the source $z_{out}$ is equal to the complex conjugate of the input impedance $z_{in}$ of the receiver as expressed by the following formula:

$$z_{in} = z^*_{out},$$

where * symbolises the complex conjugate operator.

In a preferred embodiment, it is required that the input impedance of the piezoelectric component is matched to the output impedance of the energy source (e.g. power amplifier) in the above described way. In a more preferred embodiment, the impedance is matched to be equal to a typical characteristic impedance of high frequency equipment, equal to 50Ω.

In general, a piezoelectric component in the shape of a disc or preferably focused element exhibits so called serial resonance $f_s$ as well as parallel resonance $f_p$. Those two resonances are defined by among others the thickness of the component and they are linked together, which is expressed by the following formula:

$$k_t^2 = \frac{\pi}{2} \frac{f_s}{f_p} \frac{1}{\tan\left(\frac{\pi f_s}{2 f_p}\right)},$$

where $k_t^2$ is the thickness coupling coefficient of the piezoelectric material of choice.

In the frequency ranges that are being considered, it would be advantageous to use serial resonance when the device is operating at the fundamental frequency 500. In such cases the modulus of impedance at serial resonance is in the range of hundreds of ohms (Ω), which makes it easier to match to characteristic impedance of 50Ω in contrast to impedance at parallel resonance 501, which for a component similar to the one described in Example 2, would reach impedance of tens or hundreds of kΩ for piezoelectric materials of high $Q_m$.

A component operating at higher order harmonic, e.g. third harmonic, is a lot more challenging in comparison to the one operating at fundamental frequency. Usually the impedance at serial resonance 502 is at levels of tens or hundreds of mΩ. This makes it very difficult to match to 50Ω impedance of the energy source.

Therefore, in a preferable embodiment, the piezoelectric component is driven at parallel resonance frequency 503, when operating at higher order harmonic, for example $3^{rd}$ harmonic frequency. In these preferable embodiments, the parallel impedance level is low and can reach a few Ω for components similar to those described in Example 9.

The electrical impedance matching can be achieved by several different methods using a network of passive electrical components, such as capacitors, inductors and transformers. Example 9 and Example 10 present selected impedance matching solutions.

Example 9

Figure 27:
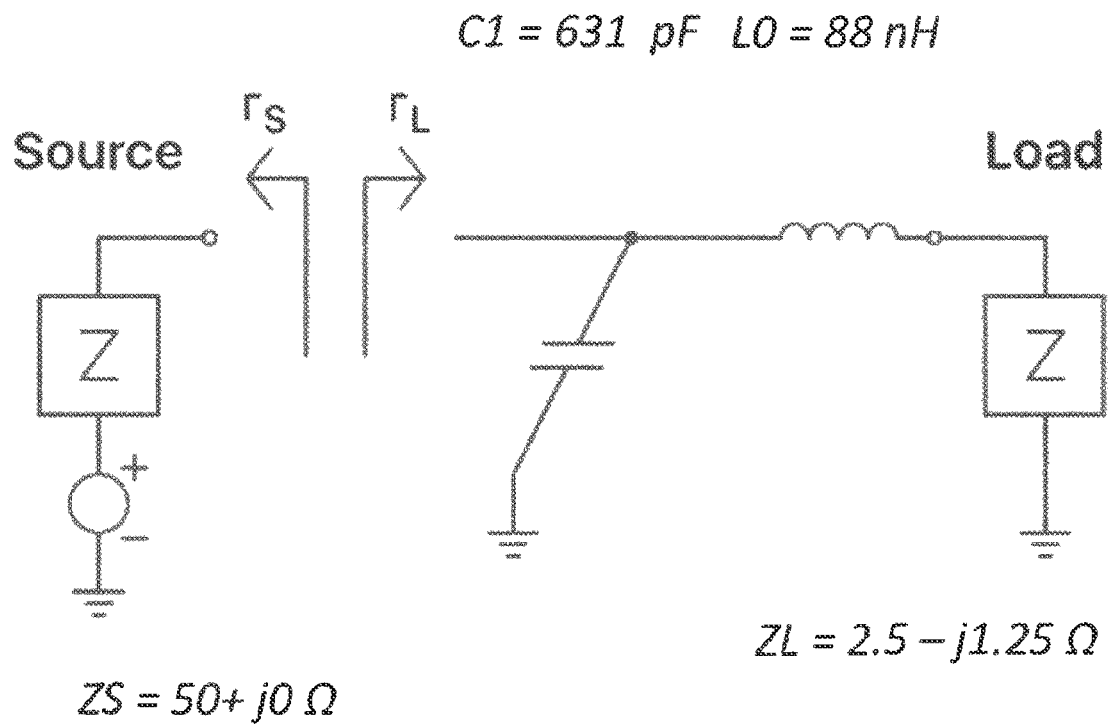
FIG. 27 is an electrical schematic of one embodiment of an impedance matching network for a focused transducer working at the $3^{rd}$ harmonic frequency based on a serial inductor and parallel capacitor.

A focused piezoelectric component exhibits a parallel resonance at the third harmonic frequency equal to 20 MHz, and it is characterised by a complex impedance of z=2.50−j1.25Ω. A matching network comprising of a serial inductor with $L_0$=88.8 nH and parallel capacitor $C_1$=622 pF will result in an impedance seen from the source of energy equal to 50Ω, as depicted in FIG. 27.

Example 10

Figure 28:
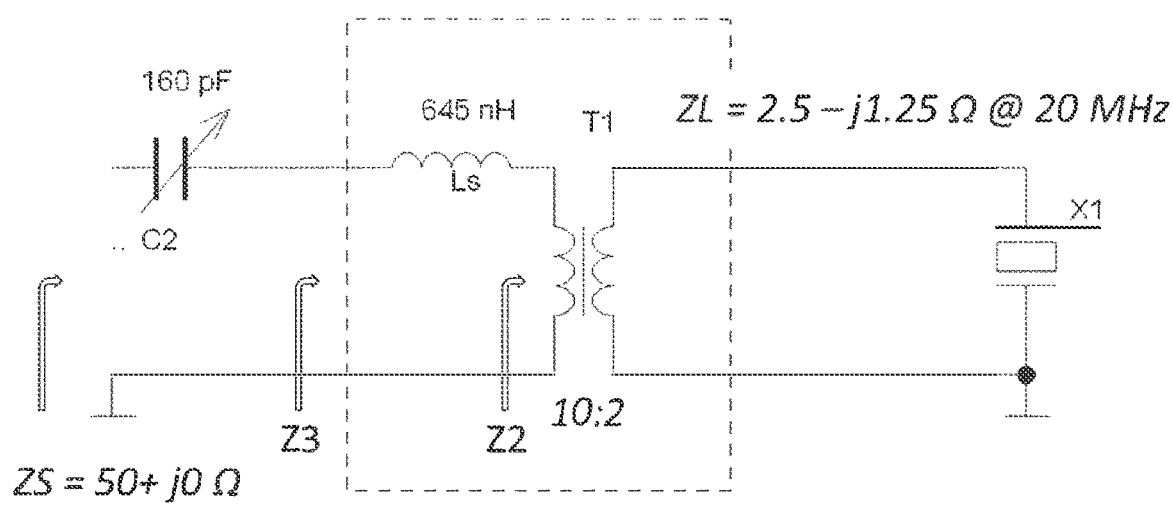
FIG. 28 is an electrical schematic of one embodiments of an impedance matching network for a focused transducer working at the $3^{rd}$ harmonic frequency based on a transformer and serial capacitor.

A focused piezoelectric component exhibits a parallel resonance at the $3^{rd}$ harmonic frequency equal to 20 MHz, and it is characterised by a complex impedance of z=2.00−j1.25Ω. A matching network comprising of a high frequency transformer T1 with turns ratio of n=5 (e.g. primary winding of 10 turns and secondary winding of 2 turns connected to the piezoelectric component) will transform the impedance seen from the secondary winding to z2=n²×(2.00−j1.25)= 50.00−j31.25. In the real circuitry, this impedance will be further affected by self and mutual inductance of the transformer inductance T1, which is represented in FIG. 28 by a lump serial inductance $L_s$=645 nH. Hence, the actual impedance seen from the primary winding of the transformer connected to a piezoelectric component taking into account the parasitic (combination of self and mutual inductance of the transformer) inductance of T1 will be equal to approximately z3=50+j49Ω. In order to bring the imaginary part of the impedance back to zero, a serial capacitor $C_2$=160 pF is added. This will result in an impedance seen from the source of energy equal to 50Ω, as depicted in FIG. 28, which will be the optimal impedance match.

In one embodiment, the electrical impedance matching network for a transducer working at the $3^{rd}$ or higher harmonic frequency consists of a number of passive electronic components such as capacitors, inductors and transformers.

In another embodiment, the electrical impedance matching network for a transducer working at the $3^{rd}$ or higher harmonic frequency consists of a serial inductor and parallel capacitor.

In preferred embodiments, the electrical impedance matching network for a transducer working at the $3^{rd}$ or higher harmonic frequency consists of a high frequency transformer with a serial capacitor. In another preferred embodiment, the serial capacitor is a variable capacitor used to fine tune the circuit.

Power Unit

Figure 29:
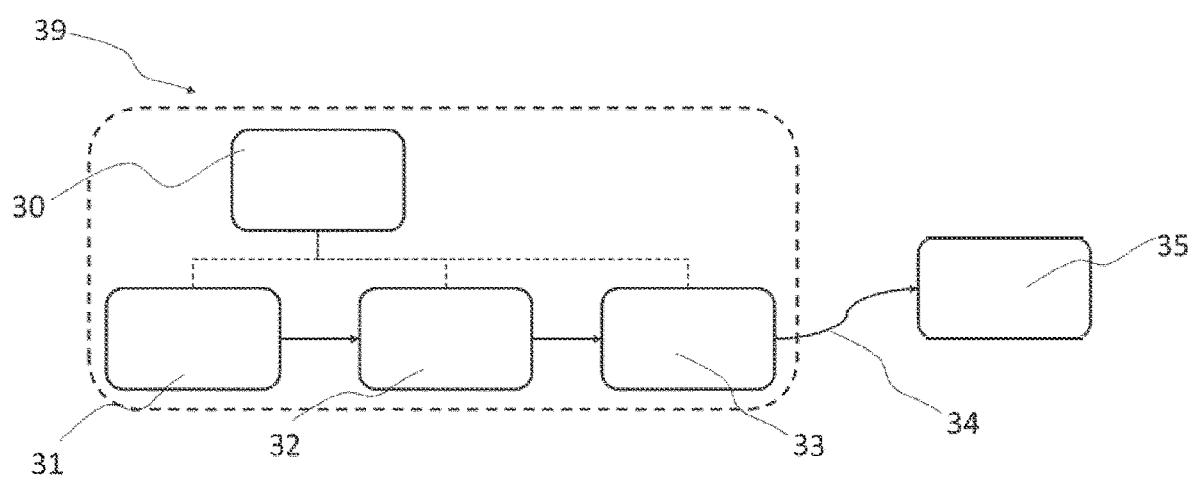
FIG. 29 is a block diagram illustrating the design and main components of one embodiment of an apparatus for tattoo removal and skin treatment.

As may be seen in FIG. 29, in one embodiment, a hand piece 35 is connected to a cable assembly 34 and driven by a power unit 39. In the embodiment shown in FIG. 29, the power unit 39 comprises: a signal generator 31, pre-amplifier 32 and power amplifier 33. The system is controlled by control unit 30, preferably consisting of a microcontroller or other computer system.

In preferred embodiments, the power unit 39 is designed to supply a specific combination of power and frequency over a pre-defined period of time in response to a trigger, for example a footswitch or similar. This is to assure the generation of a consistent pattern of lesions when used in combination with the acoustic transducer described earlier.

The control unit 30 is integrated into the system, which is constructed to select operational parameters for the systems, such as frequency and duty cycles, etc.

In a preferred embodiment, the control system includes a user interface, which allows a user to select primary operational parameters such as operational frequency, duty cycle time, output power from the transducer etc. In other embodiments, the control system will only allow the user very limited control of the operational parameters.

The selected operational parameters, whether selected by the user or as fixed settings, drive a signal generator, which generates the requested signal characteristics. Depending on the specific requirement of the signal, the signal generator 31 might not be able to provide the required power level directly without the need for an amplifier of the output signal.

In preferred embodiments, a control unit 30 is connected to a signal generator 31 to generate a specific signal frequency, burst time, power level, etc.

In one embodiment, the power unit 39 is capable of producing more than 1 W of high frequency power in a frequency range from 1 MHz to 30 MHz. In more preferred embodiments, the power unit 39 is designed so it can deliver more than 1 W of power to the impedance matched ultrasonic transducer in the frequency range from 1 to 100 MHz.

Energy of Sonification

While the focal characteristics and concentration of the ultrasound signals emitted from the piezoelectric element depends on the geometry and frequency, as illustrated in Example 7 and Example 8, the final size of the lesion created by focused ultrasound is determined by the energy of the sonification signal. The higher the energy, the bigger the volume of denaturated tissue. For example, at constant power the energy will linearly depend on time of sonification. In a simple case, the energy of a one sonification round (burst) is determined by output power P as well as the duration of the signal t adjusted for the efficiency of the electro-acoustic conversion given by $\eta$, as follows:

$$E = \eta P t.$$

Figure 30:
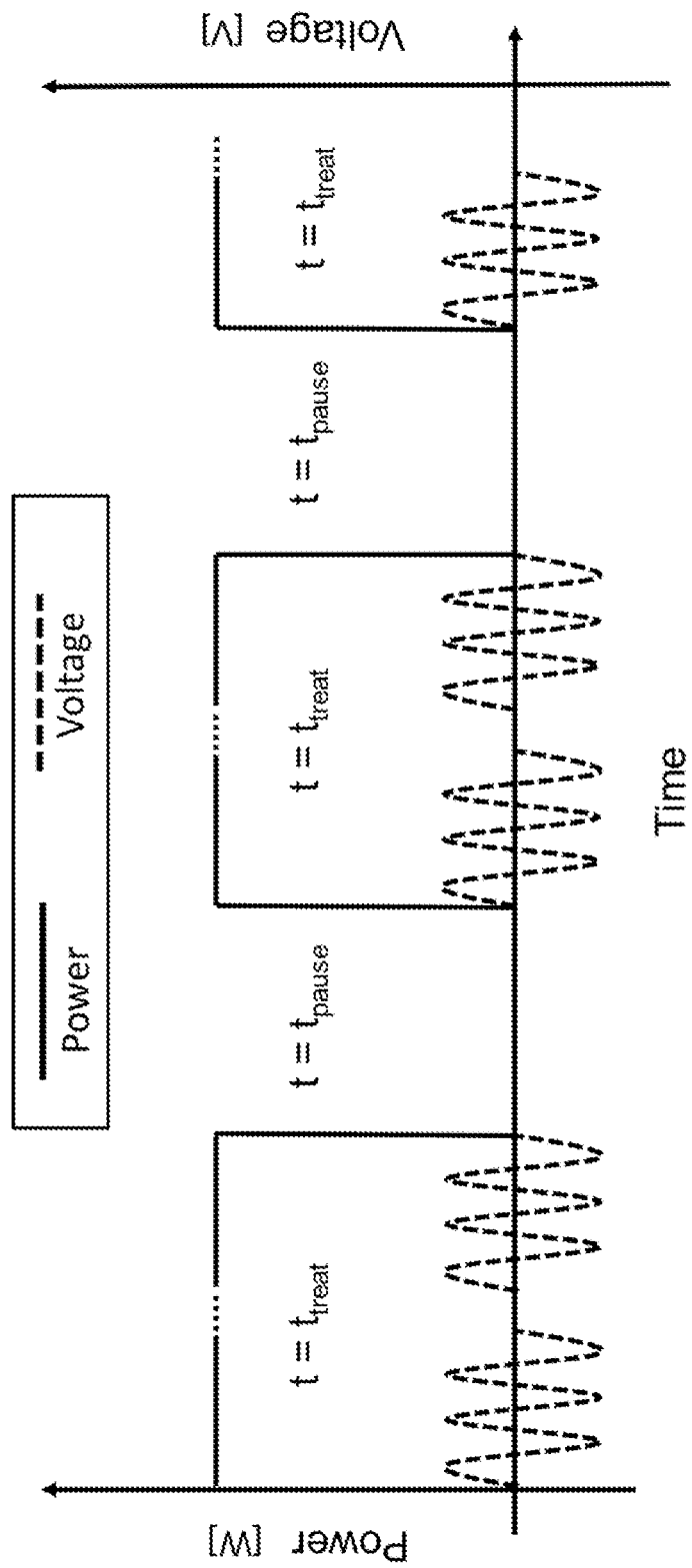
FIG. 30 is a graph of time versus power for an electrical signal generated and transmitted to the transducer.

In one embodiment, the energy is delivered in one cycle of pre-determined duration. In another embodiment, the signal can be further modulated to optimise the tattoo removal process and may be comprised of a finite number of short cycles resulting in the final energy of sonification that is the superposition of energies of each separate cycle as depicted in FIG. 30.

Lesion Creation Mechanisms

It is understood that the lesion 48 created by high intensity focused ultrasound is the result of either thermal heating or cavitation or a combination of both. Hence, the size of the lesion created in the PoT is dependent on the energy emitted from the transducer and deposited in the tissue.

In general, there is an energy threshold below which a lesion is not created, which in turn will not initiate phagocytosis. The basement membrane will furthermore not be punctured, thus preventing transport of pigments and pigment-containing cells into the epidermis. In a preferred embodiment, the deposited energy levels should be above 0.1 J.

On the other hand, too high an energy level emitted into the PoT will create excessive heating and/or cavitation, thus damaging a much larger volume of this skin than the original targeted PoT. An expanded thermal lesion will potentially extend through the Epidermis and make an open wound in the skin, thus increasing risk for infections.

Example 11

An electrically matched transducer is driven by a power unit connected. The settings in the control systems are as follows:

| Description | Symbol | Value | Unit |
| --- | --- | --- | --- |
| Peak-to-peak drive voltage | $V_{pp}$ | 100 | V |
| Characteristic impedance | R | 50 | $\Omega$ |
| Burst duration | t | 200 | ms |
| Energy conversion efficiency | $\eta$ | 0.2 | |

With these parameters one can estimate the electrical energy, $E_{el}$, from the power unit and acoustic energy, $E_{PoT}$, transmitted into the PoT:

$$V_{rms} = \frac{V_{pp}}{2\sqrt{2}} = 35.3 V$$

$$E_{el} = \frac{V_{rms}^2}{R} t = 5.0 J$$

$$E_{PoT} = \eta E_{el} = 1 J$$

In some embodiments, an acoustic energy level transmitted from the transducer is between 0.01 J to 100 J delivered at a burst duration of 1 to 100000 ms. In other embodiments, an acoustic energy level transmitted from the transducer is between 0.1 J to 25 J delivered at a burst duration of no more than 5000 ms. In preferred embodiments, an acoustic energy level transmitted from the transducer is between 0.1 J to 10 J delivered at a burst duration between 1 ms and 2000 ms. In still yet other embodiments, the acoustic energy level transmitted from the transducer can be continuous at an acoustic power level of 1 W to 100 W.

In order to create a lesion around and within the focal zone, a certain threshold of acoustic energy density and/or acoustic intensity needs to be reached. It is useful to define an average acoustic energy density around 6 dB focal zone as follows:

$$\hat{u} = \frac{E_{POT}}{\pi (LD/2)^2} \times \beta,$$

where $\beta$ is a shape factor accounting for the fact that not all energy is focused within 6 dB focal zone. For the pressure distribution given in FIG. 24, this factor is around 65%-72%. Equally, an average acoustic intensity within 6 dB focal zone can be defined as:

$$\hat{I} = \frac{P_{POT}}{\pi (LD/2)^2} \times \beta.$$

$P_{PoT}$ is the acoustic power transmitted by the transducer into the focal point. Depending on the sonification conditions the lesion can be produced primarily by thermal heating of the tissue to temperatures of above 42° C. In this case a certain energy density threshold needs to be reached. At high acoustic intensities the lesions are created primarily by cavitation. One can also expect a combined thermal and mechanical effect at simultaneously occurring high acoustic intensity and high energy density.

Combinations of acoustic power, burst duration and driving frequency result in different types of energy transfer functionality and lesion size created in and around the 6 dB focal zone as defined above and calculated in Example 7 and Example 8. Using the same assumptions regarding the F-Number and speed of sound in water as in these examples, the resulting lesion shape and size can be estimated as shown in Example 12.

Example 12

| Treatm. | Freq MHz | Acoust. Power W | Burst dur. ms | Acoustic Energy J | 6 dB Focal diam µm | 6 dB Focal depth µm | Average Acoust. Intensity kW/cm$^2$ | Average Acoust. Energy Dens kJ/cm$^2$ | Lesion diam. (Est) µm | Lesion length (Est) µm | Primary Phys. Process |
|---|---|---|---|---|---|---|---|---|---|---|---|
| A | 20 | 10 | 100 | 1.0 | 80 | 403 | 140 | 14.0 | 80 | 400 | Thermal |
| B | 20 | 5 | 100 | 0.5 | 80 | 403 | 70 | 7.0 | 40 | 200 | Thermal |
| C | 20 | 1 | 100 | 0.1 | 80 | 403 | 14 | 1.4 | — | — | No lesion |
| D | 20 | 20 | 100 | 2.0 | 80 | 403 | 279 | 27.9 | 200 | 500 | Combined |
| E | 20 | 40 | 5 | 0.2 | 80 | 403 | 558 | 2.8 | 500 | 500 | Cavitation |
| F | 20 | 10 | 500 | 5.0 | 80 | 403 | 140 | 69.8 | 150 | 800 | Thermal |
| G | 20 | 10 | 1000 | 10.0 | 80 | 403 | 140 | 139.5 | 300 | 1600 | Thermal |
| H | 6.66 | 10 | 100 | 1.0 | 240 | 1210 | 15 | 1.5 | — | — | No lesion |
| I | 6.66 | 45 | 100 | 4.5 | 240 | 1210 | 70 | 7.0 | 300 | 1500 | Thermal |
| J | 6.66 | 45 | 500 | 22.5 | 240 | 1210 | 70 | 34.8 | 1200 | 6000 | Thermal |

In preferred embodiments, a combination of settings is selected to create a lesion in and around the focal zone characterized by a diameter in the plane perpendicular to the central axis in the range of 0.01 mm and 2.0 mm and a length in the plane along the central axis in the range of 0.01 mm and 4.0 mm. In other embodiments the lesion in and around the focal zone is characterized by a diameter in the plane perpendicular to the central axis in the range of 0.01 mm and 1.0 mm and a length in the plane along the central axis in the range of 0.1 mm and 2.0 mm. In preferred embodiments, the lesion in and around the focal zone is characterized by a diameter in the plane perpendicular to the central axis in the range of 0.03 mm and 0.6 mm and a length in the plane along the central axis in the range of 0.2 mm and 1.5 mm.

Treatment Methodology

In order to obtain removal of tattoos with pigments distributed over larger areas of the body, it is necessary to consider the effect of the sonification time for each lesion compared with a process of several repeated shorter sonifications.

Figure 31:
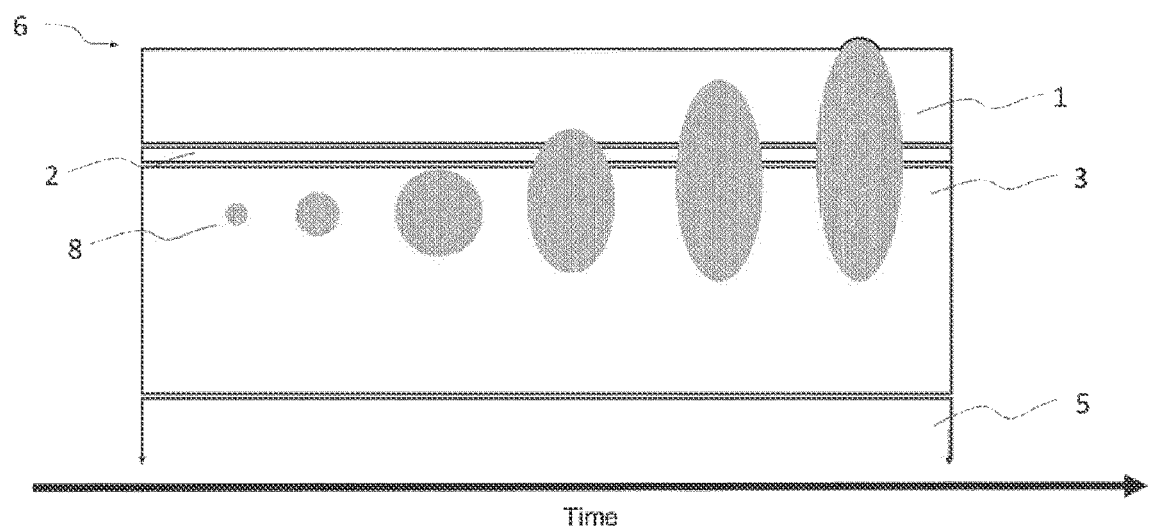
FIG. 31 a graph illustrating the relative expansion of lesion size when the time is increased at a PoT for a constant power level.

Due to several effects of the sonification including convection and increased attenuation etc. a prolonged sonification time on a single area will lead to elongated lesion points toward the surface of the skin and not extending into the deeper part of the subcutaneous layer of the skin 4 as illustrated in FIG. 31 and Example 12.

In order to cover a large area of treatment (bigger than one lesion point) more than one POT is required. In different embodiments of methods of treating the skin, these PoTs may be patterned or placed in various different ways in order to achieve the best results. In one embodiment, separate PoTs are spaced laterally to create lesions in an appropriate pattern with 0.1 mm to 5 mm spacing between the circumference of each lesion. In other embodiments, the distance between the circumference of each lesion in the pattern is separated by no more than 4 mm spacing. In preferred embodiments each lesion is separated with no more than 2 mm.

Figure 32:
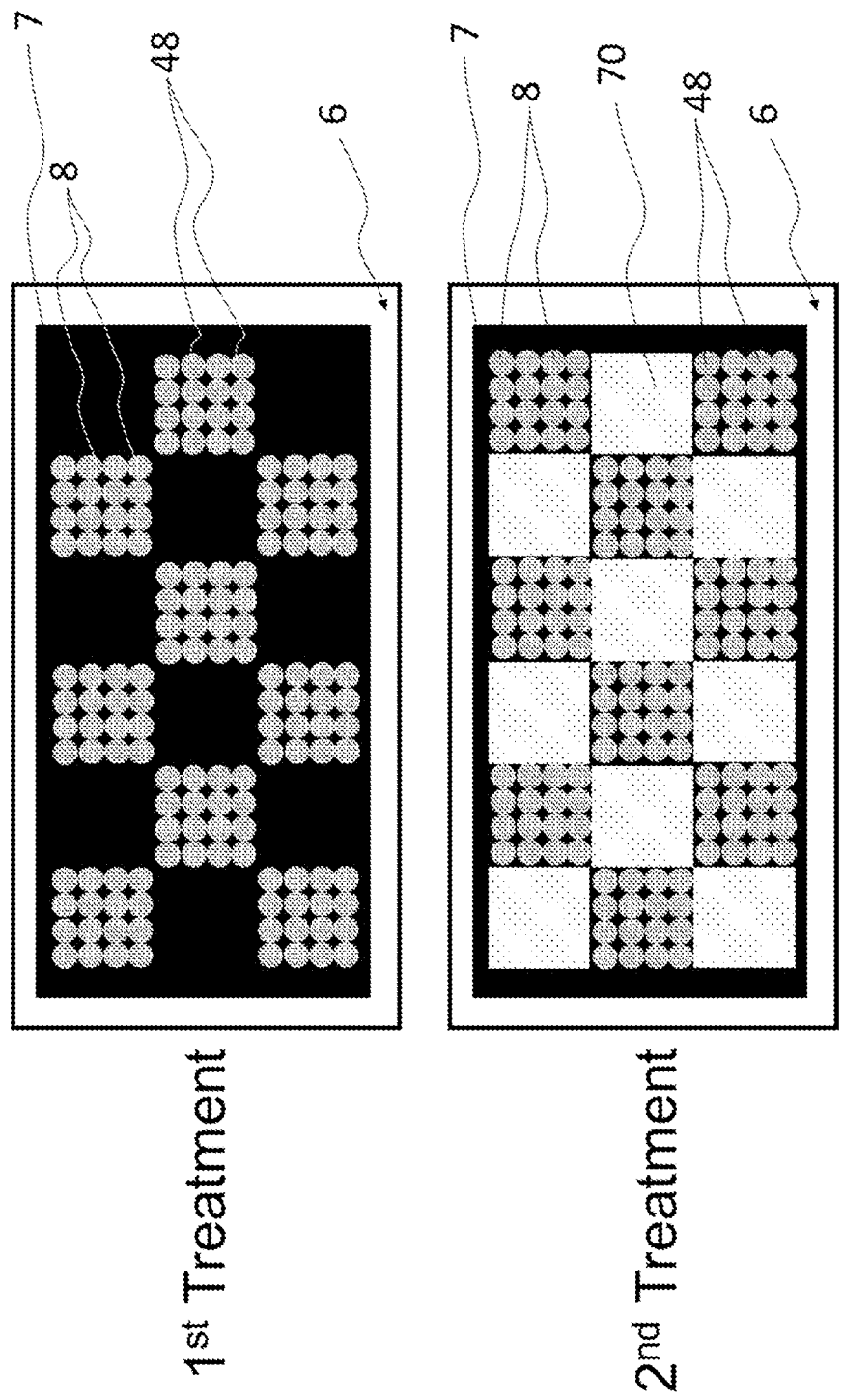
FIG. 32 illustrates and example of a treatment strategy, where a tattooed area is treated in an interlaced pattern resembling a checkerboard pattern.

In some embodiments an intermittent pattern of 1 mm$^2$ to 1000 mm$^2$ treatment areas are interlaced with untreated areas of similar size. In a preferred embodiment, shown in FIG. 32, an intermittent pattern of 1 mm$^2$ to 25 mm$^2$ treatment areas are interlaced with untreated areas of similar size, for example in the form of a checkerboard or hexagonal pattern or similar. In another embodiment, the sonification is administered in a semi- or fully-continuous way. This means that the energy is deposited at rates that match the motion of the hand-piece.

Figure 33:
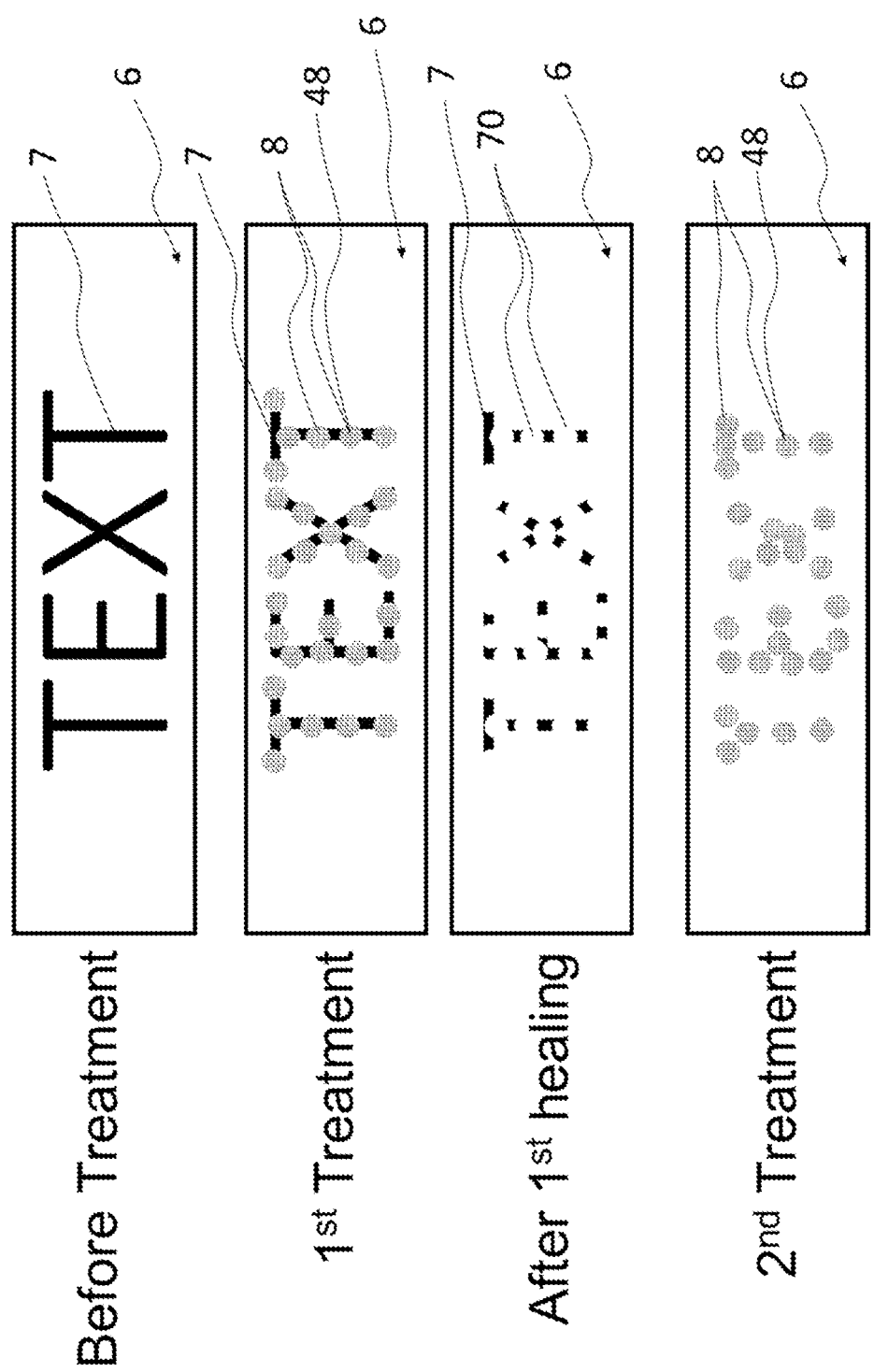
FIG. 33 illustrated an example of a treatment strategy, where fine-pitch tattoos are treated in an interlaced pattern.

The selected pattern and treatment methodology of PoTs on a selected area on the skin must potentially be repeated several times to cover all targeted areas and gradually decrease the concentration of pigments in the skin. If a treatment method is used that incorporates interlaced or spaced PoTs, such as in a checkboard pattern or similar, subsequent treatments should be used on the untreated areas and skip over the previously treated areas to complete the coverage over the continuous area. In this way, subsequent treatments may be alternated between treated and untreated areas within the same overall treatment area. An example of a treatment strategy for a tattoo containing text or other fine-pitch graphical elements is shown in FIG. 33. Preferably, treatments are performed at intervals where the different functionalities for pigment removal have had sufficient time to be completed, and possible redistribution of pigments has had time to take place within the skin.

In preferred embodiments, treatment sessions in which several PoTs is repeated at intervals allowing 1 to 12 weeks between each treatment session depending on the age and other characteristics of the skin as well as the treatment settings as illustrated in Example 13.

Example 13

| Treatment | Treat. Area mm$^2$ | XY Spacing mm | Energy J | Freq MHz | PoT depth mm | Pattern | Session Interval weeks |
|---|---|---|---|---|---|---|---|
| A | 5 × 5 | 1.2 | 1 J | 20 | 1.0 | Checkerb. | 4-5 |
| B | 5 × 5 | 1.2 | 2 J | 20 | 1.0 | Checkerb. | 5-6 |
| C | 5 × 5 | 1.2 | 1 J | 20 | 1.5 | Checkerb. | 5-6 |
| D | 5 × 5 | 1.2 | 1 J | 20 | 2.0 | Checkerb. | 7-8 |
| E | 10 × 10 | 1.2 | 1 J | 20 | 1.0 | Checkerb. | 8-10 |
| F | 5 × 5 | 0.8 | 1 J | 30 | 1.0 | Checkerb. | 3-4 |
| G | 5 × 5 | 1.2 | 1 J | 20 | 1.0 | Hexagon | 3-4 |
| H | 3 × 3 | 1.2 | 1 J | 20 | 1.0 | Checkerb. | 2-3 |

Disposable Transducer Heads

Figure 34:
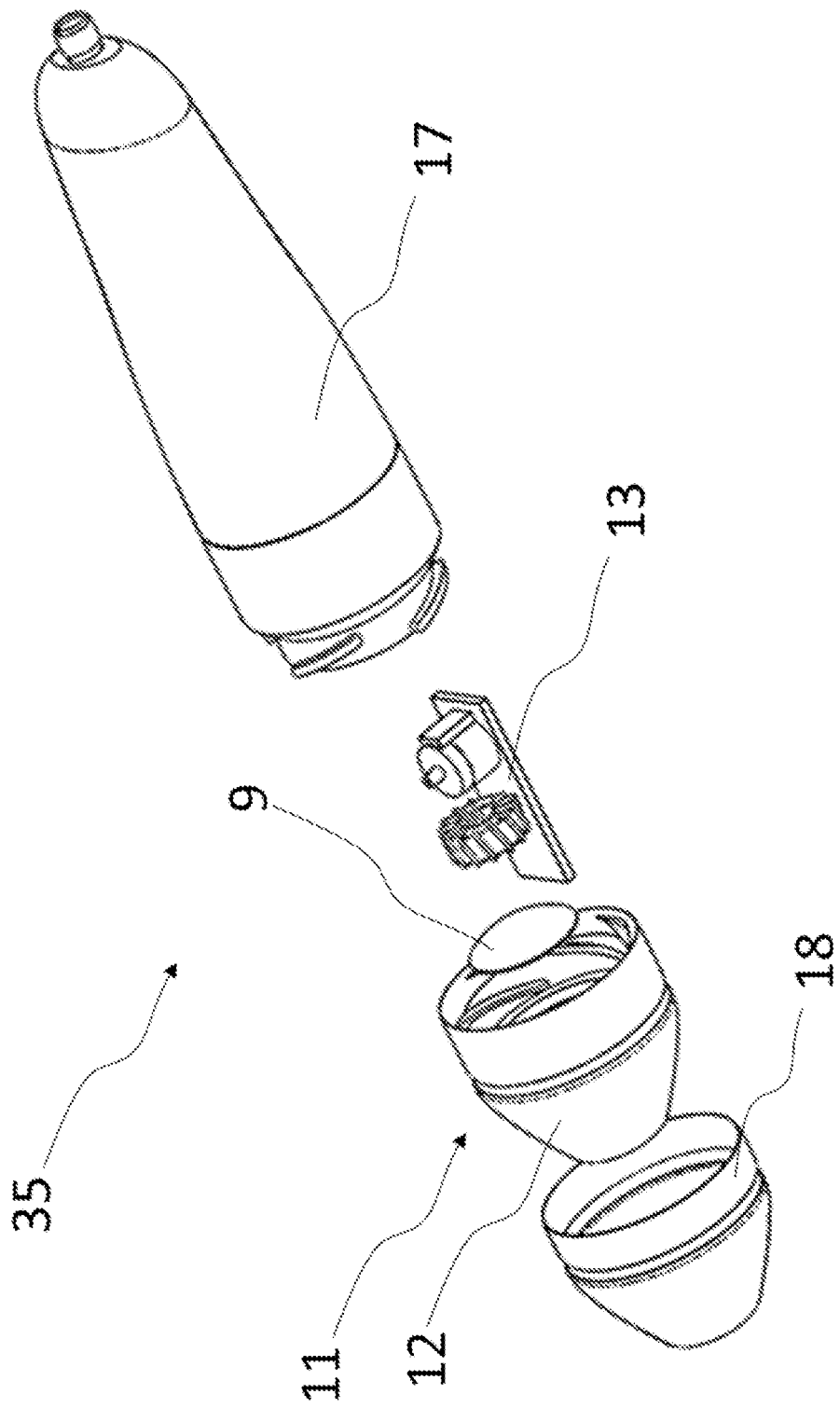
FIG. 34 illustrates an exploded isometric view of one embodiment of a hand piece with easy to replace ultrasonic transducer for skin treatment.

FIG. 34 illustrates an exploded isometric view of one embodiment of a hand piece with easy to replace ultrasonic transducer head 11. With the repeated emission of the power-bursts at levels mentioned above, ageing might be a problem in the piezoelectric element. Ageing in piezoelectric materials and transducers are inherently difficult to predict accurately as it is related to many externally independent factors such as drive voltage, frequency, temperature, mechanical stresses, corrosion condition and any combination of these.

To secure predictable conversion efficacy between the electrical signal transmitted to the transducer to the acoustic signal received at the PoT, the piezoelectric element and part of the transducer may need to be replaced at regular intervals. In some embodiments, a specifically designed algorithm may be used to predict the life time of the replaceable transducer and inform the user.

In preferred embodiments, the hand piece 35 is designed in a way to make it is easy to replace transducers when needed. The replaceable transducer 11 should preferably comprise the piezoelectric element 9, housing 12 and integrated electrical matching circuit 13. The transducer head 11 includes a releasable coupling interface that mates with the rest of the hand piece containing camera, optics, connectors, cables and electronic components. In the embodiment shown in FIG. 34, a threaded interface is used but other interfaces may be used such as interference fit, fasteners etc.

In another preferred embodiment, the transducer comprises a device for monitoring of usage and a function to deactivate the transducer when a pre-set limit is exceeded. The monitoring could for example be, but not limited to, signal cycle count, active treatment time or measurement of reflected electrical energy.

Optical Monitoring

It is beneficial for the method to include additional optical monitoring systems aiding the user administrating the skin treatment and in particular the tattoo removal procedure with proper optical feedback. By allowing the user of the device to view the treated area of the skin, a more accurate placement of the PoT may be achieved. This can improve accuracy of the treatment and shorten the treatment time and number of necessary repetitive treatments to fully remove a tattoo.

Figure 35:
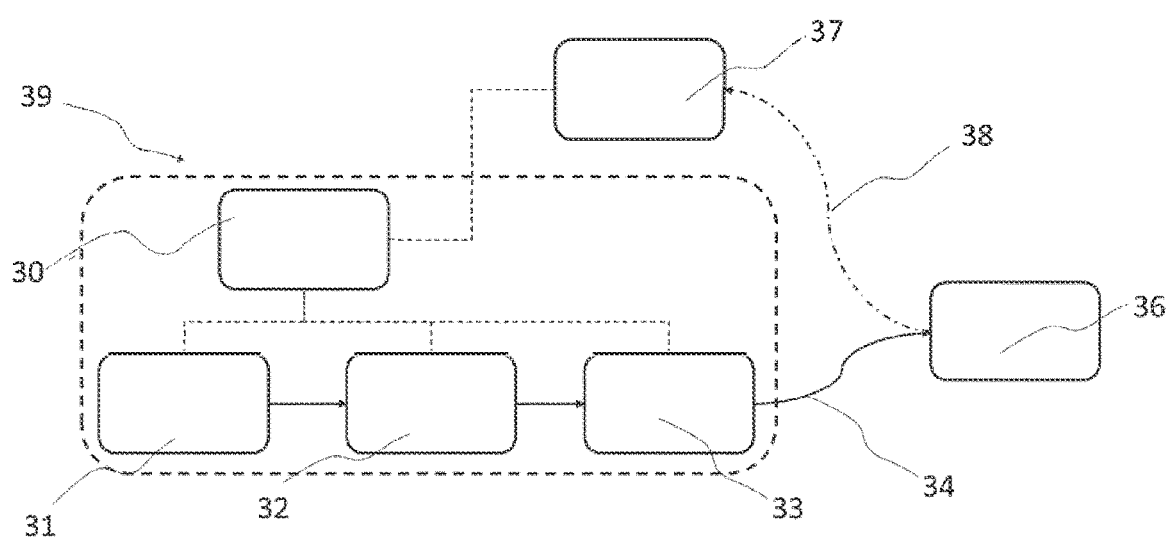
FIG. 35 is a block diagram illustrating the design and main components of one embodiment of an apparatus for tattoo removal and skin treatment with optical monitoring.
Figure 36:
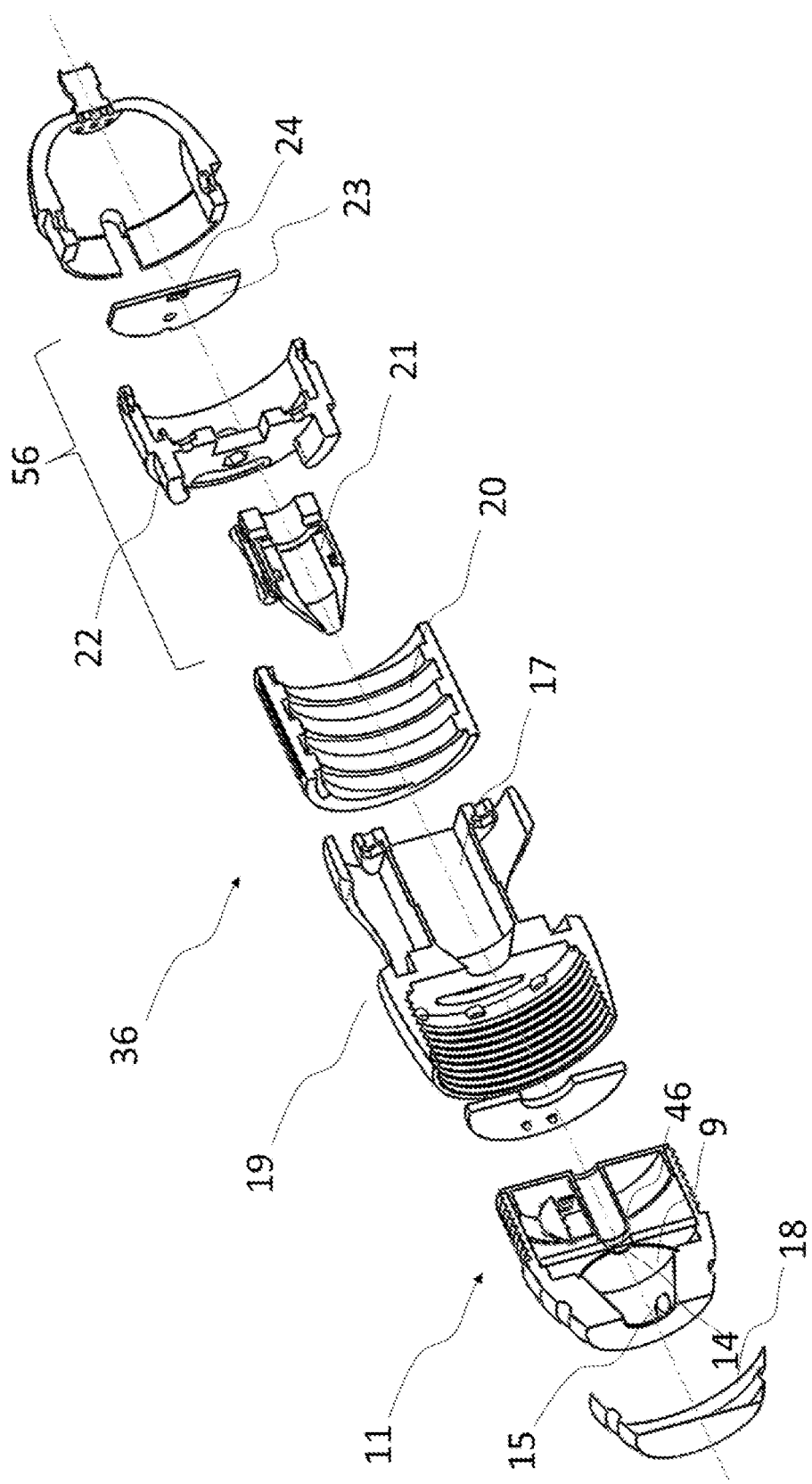
FIG. 36 illustrates an exploded isometric section view of one embodiment of a hand piece with an easy to replace ultrasonic transducer comprising optical monitoring system as well as adjustable optical focus objective.

FIGS. 35 and 36 illustrate one embodiment of a hand piece 36, that includes an optical system comprising components 21, 22, 23, 24. The optical system 36, which is integrated with the acoustic transducer 11, provides visual information regarding the location of the placement of the PoT below the skin. In some embodiments, the hand piece 36 is equipped with a light source 15 to properly illuminate the skin surface as depicted in FIG. 13, FIG. 14 and FIG. 17. In one embodiment, the light source 15 is constituted by one or more bulbs. In the preferred embodiment, a LED (light emitting diode) or a multiple of LEDs are used as a light source 15.

Returning to FIG. 13, it may be appreciated that in the embodiment shown in FIG. 13, two light sources 15 are used. Depending on the embodiment, any number of light sources may be used including a single light source 15 or a plurality of light sources 15. In the embodiment shown in FIG. 13, the light sources extend down the outside walls of the cavity 52 such that only their tips protruded into the cavity 52. Accordingly, the walls of the cavity 52 may have one or more light source openings. This allows the light from the light sources 15 to illuminate the coupling medium 40 and consequently, the surface of the skin above the PoT. In a preferred embodiment, the light sources 15 are sealed with an O-ring or other type of seal to the wall of the cavity 52 such that the coupling medium 40 cannot escape the cavity 52 via the light source opening.

In yet other embodiments, the light source 15 may be located outside the cavity walls. In particular, the light source may be integrated behind the acoustic generating device 9 and shine down through the same opening 14 designed to allow the optical system to image the surface of the skin above the PoT 8. This provides a simplified design as it creates less openings in the cavity 52 for the coupling medium to potentially escape from.

As already discussed with respect to FIG. 15, some embodiments of the hand-held device 36 may include an optical monitoring system 56. FIG. 36 illustrates an exploded isometric section view of one embodiment of a hand piece 36 with an easy to replace ultrasonic transducer 11 comprising an optical monitoring system 56 with an adjustable optical focus objective. In some embodiments, an optical monitoring system 56 for representation of the optical signal is integrated into the hand piece and transducer, thus providing easy visibility for the operator of the apparatus during treatment. The monitoring system may use any number of optical components including but not limited to lenses, displays, CCD's, arrays and or fiber optic image conduits to name a few.

In a preferred embodiment, the optical monitoring system is integrated in the hand piece concentrically with the focused piezoelectric element, i.e. the optical axis of the optical system is aligned with longitudinal axis of the hand piece 36 and/or with the axis of symmetry of the focused transducer that passes through the PoT. In such embodiments, the focused piezoelectric element is designed to have a hole in the center, which physically allows the optical signal to pass from the skin 6 to the image sensor through a system of lenses as depicted in FIG. 36.

Preferably, the optical system is protected from the liquid contents of the medium 40 by a transparent pathway 41 as shown in FIG. 17. In one embodiment, the transparent pathway 41 separates the medium 40 from the optical system by a thin optically transparent separator 46 made from polyethylene, polypropylene, polycarbonate, polyester, epoxy and the like. The transparent pathway 41 may be subsequently fixated and made water-tight by an appropriate glue.

In some embodiments, the transparent pathway 41 between the optical system and medium is made with a 0.01-10 mm silicate or borate glass. In a preferred embodiment, the transparent pathway 41 between the optical system 56 and medium 40 is made with a 0.05-0.3 mm silicate or borate glass.

As may be seen in FIG. 36, the optical monitoring system 56 may include an image sensor 24. The image sensor 24 may be mounted with image sensor support electronics 23. In typical embodiments, the image sensor support electronics will be mounted along with the image sensor 24 on a PCB board. As is known in the art, the image sensor support electronics provide the necessary support for the image sensor 24 including power, power conditioning, signal and signal conditioning and any required drivers. In some embodiments, the image sensor 24 is a CMOS sensor, and in other embodiments, the image sensor 24 is a CCD camera or any other device that can convert images into an electric or digital signal. In some embodiments, no image sensor 24 is included and the optical monitoring system allows imaging of the surface of the skin above the PoT directly on the operators eye via a system of lenses.

In systems that do include an image sensor 24, it is necessary to match the field of view and resolution in the optical system with both the type of optical imaging sensor 24 and its resolution. This may be done be selecting imaging sensors 24 of the correct pixel size and pixel count and paring them with the correct type of optical lenses 25, as well as adjusting the distances between these individual components.

As may be seen in FIG. 36, the system 36 may include a lens holder 21. The lens holder 21 resides along the optical axis, in this case the longitudinal axis, and contains one or more lenses that are fixed with respect to lens holder 21. As may be seen in FIG. 34, the lens holder has a hole through the middle down the optical axis. In addition to the lens holder 21, the optical monitoring system 56 may also have a image sensor holder 22. In preferred embodiments, the image sensor 24 is affixed to the image sensor holder 22. In operation, either the image sensor holder 22, or the lens holder 21 is designed to be able to translate along the optical axis with respect to the other component. This allows adjustment of the focal point of the lens with respect to the image sensor and allows focussing.

In preferred embodiments, the optical monitoring system 56 includes a threaded interface 20 wherein the threads run longitudinally along the optical axis. The threaded interface is coupled to either the lens holder 21 or the image sensor holder 22 such that when the threaded interface 20 is rotated, either the lens holder 21 or the images sensor holder 22 is caused to traverse the optical axis. The translation along the optical axis changes the relative distance between the lens holder 21 and the sensor holder 22 and allows the surface of the skin above the PoT to be imaged.

As may be appreciated, the optical monitoring system 56 may include other components including additional lenses or other optical components. Regardless, an integrated optical monitoring system 56 requires an optical path to traverse the entire hand held device from the image sensor 24 all the way to the surface of the skin above the PoT.

In some embodiments, the image sensor 24 is located between 0 to 500 mm from the acoustic generating element 9 and comprise a set of 1 or more optical lenses 25 to provide a focus on the surface of the skin above the PoT as shown in FIG. 15.

In one embodiment the focus of the optical system is adjusted such that the field of view through the hole in the element covers a visible area between 1×1 mm$^2$ and 100×100 mm$^2$. In a preferred embodiment the optical system provides a picture through the hole in the focused transducer 9, which is 10×15 mm$^2$ in size, and has a resolution not less than 20 µm.

Although, the optical system is shown along the longitudinal axis in the embodiments above, the optical system may also be off axis. The important thing is that the field of view is the surface of the skin above the PoT. To this end, systems that include an off axis optical system are envisioned. Such systems may be partially or totally off axis. For example, one or more mirrors could be used in the optical monitoring system to steer the image around and create an optical path that is not linear.

Example 14

A 2 megapixel 1/2.7" CMOS sensor with a pixel size of 3×3 µm$^2$ is mounted with an optical lens characterized by a focal length of 10 mm, an aperture of 2.0 mm, a field of view of 37.5 degrees, and a F-number of 1.6. At a working distance of approximately 15 mm between the lens 25 and the hole in the element 9, and a further 10-15 mm between the hole in the element 9 and the surface of the transducer 45, a resolution of approximately 5 µm and a field of view of around 7×11 mm$^2$ in size can be obtained.

In preferred embodiments, the hand-held assembly 36 includes a second housing 19 that couples the optical monitoring assembly 56 with the transducer head 11. In the embodiment shown in FIG. 36, the transducer head 11 is coupled to the second housing 19 via threads. Accordingly, the transducer head 11 may be easily removed from the second housing 19 by simply unscrewing it. Accordingly, a second transducer head (not pictured) may be easily swapped in place. The second transducer head may have a different acoustic monitoring device with different parameters or may simply just be a newer version of the transducer head 11 it is replacing.

During some treatments, it may be useful to use other excitation and reception wavelengths in the optical system than those used for normal visible light having a wavelength range of approximately 400 nm to 700 nm. In some embodiments, the transducer system is arranged with the light source 15 having an emission wavelength starting in the ultraviolet spectrum of approximately 290 nm. In yet other embodiments, the light source 15 is selected to have an emission range that extends into the infra-red spectrum, up to approximately 1100 nm. In other embodiments, the light source 15 has a broad emission range that extends from the ultraviolet spectrum to the infrared spectrum.

In one embodiment, the camera system is selected to be able to detect wavelengths ranging into the ultraviolet spectrum as stated in one of the embodiments above. In other embodiments, the camera system is selected to be able to detect a wavelength ranging into the infrared spectrum as stated in one of the embodiments above. In yet other embodiments, the camera is selected to be able to detect the full range from 290 nm ultraviolet light to infrared light up to 1100 nm.

Figure 37:
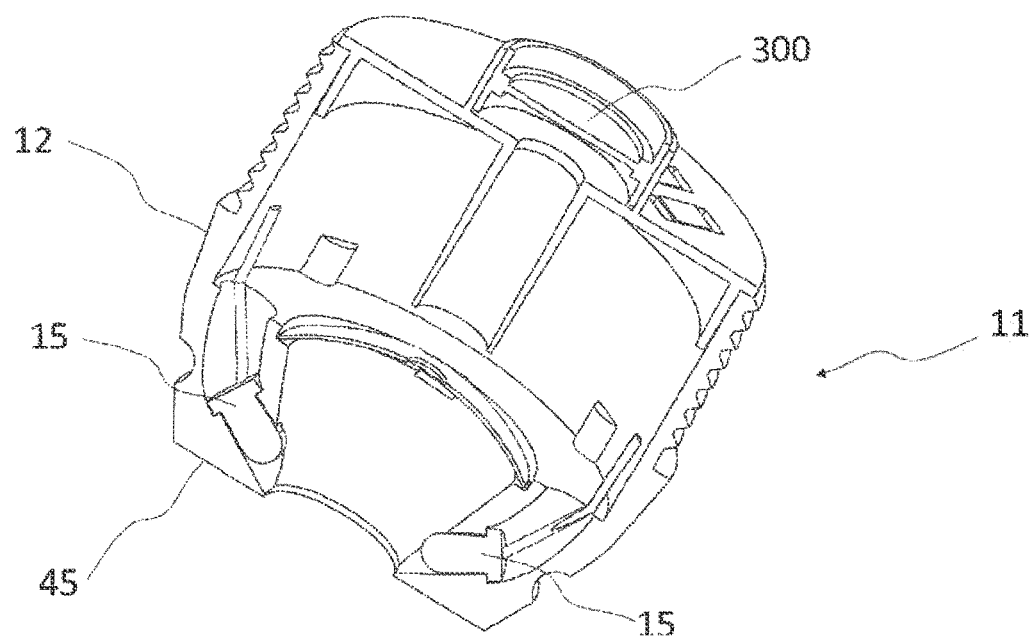
FIG. 37 illustrates an isometric section view of a transducer head with an integrated optical filter that allows the wavelengths of received light to be selectively filtered by the optical monitoring system.

FIG. 37 illustrates an isometric section view of a transducer head 11 with an integrated optical filter 300 that allows the wavelengths of received light to be selectively filtered by the optical monitoring system. In embodiments that include an optical monitoring assembly, one or more optical filters 300 can be incorporated into the optical path, whereby only selective wavelengths are detected by the camera. In these embodiments, the light source 15 is used in combination with a filter 300, which ensures that the camera system primarily receives wavelengths outside the emission spectrum of the light source. In this configuration, fluorescent pigments or areas in the PoT 8 can be more easily visualized.

In the embodiment shown in FIG. 37, the optical filter 300 is integrated into the transducer head 11. This means that when the transducer head 11 is removed or changed, the optical filter 300 will also be changed. Because the optical filter 300 will often be matched with the wavelength of the light source 15, embodiments preferably mount them on the same portion of the assembly such that they stay together. However, in other embodiments, the optical filter 300 may be mounted on other parts of the handheld assembly. For example, the optical filter 300 may be integrated into the optical assembly 56.

As may be seen by returning to FIG. 35, in some embodiments, the visual information is transmitted to the control unit 37 via a link 38. Link 38 may be a wired or wireless connection. Preferred systems will use a wireless link 38. The visual information may then be displayed on a monitor integrated within the hand-held device. If the monitor is integrated into the hand-held device it will need to be of a restricted size. A small LCD display would work for example. In other embodiments, the monitoring system is separate from the hand-held device and may be connected to, or provided by, a separate computer. Accordingly, the monitor could be much bigger such as a large flat panel monitor or TV. In yet other embodiments, combinations of the above monitoring systems may be used.

Various Scanning Functionalities

During the tattoo removal procedure both large uniformly tattooed areas and very fine lines of tattoo pigment may need to be removed. A treatment strategy for dealing with both extremes might therefore be relevant. A treatment to handle both types of tattooed areas could be obtained by changing the transducer types manually to have the optimum transducer type in terms of focus size, depth and frequency. In other embodiments, this may be achieved by including different scanning and physical manipulations in the transducer or methods of treatment.

In some embodiments, a mechanical scanning function is integrated into the transducer providing several separate PoTs from one contact-point on the skin. In some embodiments, the scanning function may be used to move the PoT in both X-, Y- and Z directions. In other embodiments, the mechanical scanning integrated in the transducer is used to continuously move the PoT over the surface of dermis to provide a continuous lesion. In some embodiments, the mechanical scanning function is an external robot which operates the transducer. In yet other embodiments, a specific image analysis algorithm is used to control the mechanical scanning function to systematically move the PoT for optimized treatment. The image analysis algorithm may receive images from the optical monitoring system integrated into the system. The image analysis program would analyse the received images and determine the area for treatment and proceed accordingly.

Other Applications of the Method.

The method and apparatus described above is concentrated on tattoo removal. The methods and apparatus are however not limited to this, but can also be applied for other indications and areas.

In some embodiments, the functionality described herein is used to remove warts on the skin, typically characterized by cells infected with a type of human papillomavirus (HPV), such as verruca vulgaris, verruca plana, verruca acuminate, and verruca plantaris. Returning to FIG. 6, in embodiments of wart removal, a series of lesions 8 are positioned closely together in order to cover the area of the skin 6 containing the wart. The lesions will open the basement membrane 2, denaturate and coagulate the protein content in the dermis 3 and epidermis 1, where the wart is located, and thereby decrease the internal adhesion between cells in the dermis and epidermis around the boundary of the PoT 8. A volume of isolated cells 100 containing the affected cells will therefore be formed similar to that illustrated in FIG. 7. After some time, the body will excrete the isolated and disconnected cells 100 as illustrated in FIG. 8. The normal healing process will subsequently replace excreted cells in the dermis 3 and epidermis 2 with new HPV-virus free cells as illustrated in FIG. 9.

Figure 38:
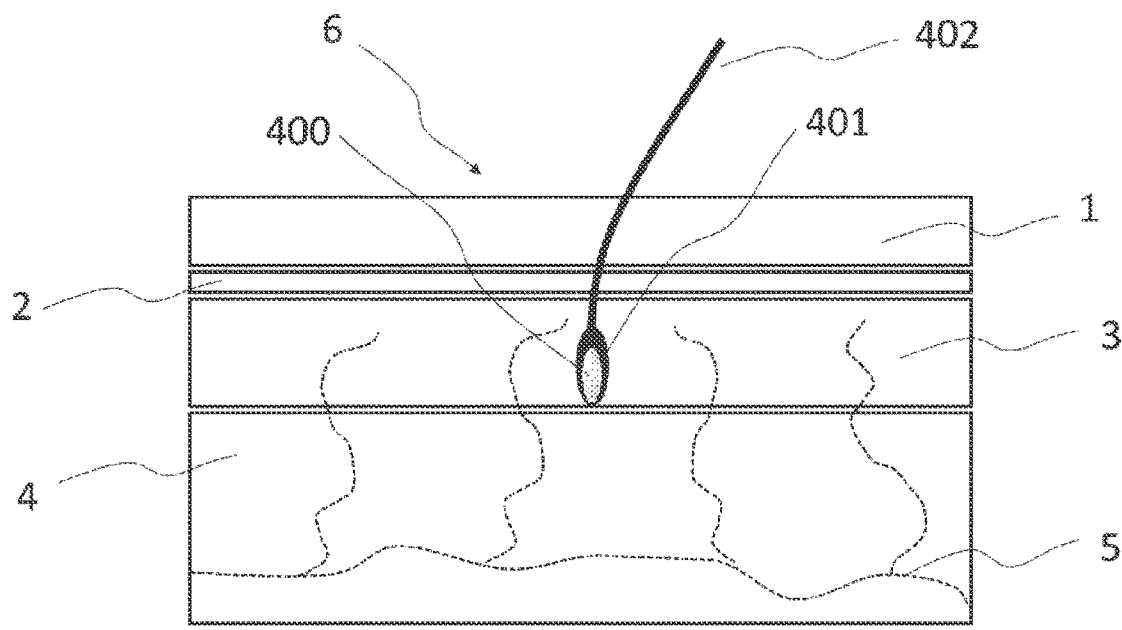
FIG. 38 depicts a cross-section of the skin including a human hair.

In another application, the methods taught herein may be used for permanent removal of unwanted hair. Referring to FIG. 38, in these embodiments, a PoT 8 is positioned in the location of a bulb 400 and papilla 401 of a hair 402. These features are typically located at, or near, the boundary between the dermis 3 and subcutaneous 4 layers, and can therefore be located relatively accurately using the optical system illustrated in FIG. 15, FIG. 17 and FIG. 36. The damaged cells in the PoT will be removed by the lymphatic system 5 through phagocytosis as illustrated in FIG. 5. It is known that the cells responsible for growth and re-growth of hairs are located in and around the papilla of the hair 400, and that these do not regenerate naturally once removed from the skin. During the healing of a lesion in this area created by the present method, new hair is therefore not regenerated by the human body, and a permanent hair removal can thereby be obtained.

In another embodiment, the method is used to treat various cancer conditions located in or close to the skin. Examples of such conditions are, but not limited to, malignant melanoma, squamous cell carcinoma, basal skin carcinoma, lymphomas and breast cancer. In embodiments for treating cancer, the basic functionalities of the method are similar to those illustrated by FIG. 2 to FIG. 9. Lesions are positioned inside the affected area, whereby all three functionalities of direct excretion and lymphatic removal may occur to remove malignant cells and replace them with healthy cells after the healing process has been completed. These methods may be used in combination with other pharmaceutical treatments, such as chemotherapy and/or antibody treatments etc. In these types of treatments, the imaging system illustrated in FIG. 37 may be used to selectively image and treat fluorescent areas generated by various functional molecules incorporated in the pharmaceuticals. In some embodiments, the method may be used at a low energy setting to selectively increase the temperature by 10 to 15 K inside a well-defined area and thereby increase specific pharmaceutical efficiency.

In other embodiments, the methods may be used to treat more benign conditions such as, but not limited to, hyperpigmentation, birthmarks, actinic keratosis, rosacea, telangiectasias, common scarring, psoriasis, solar lentigo, striae etc. In these embodiments, a series of lesions 8 are positioned closely together in order to cover the affected area of the skin 6 as illustrated in FIG. 6. The lesions will open the basement membrane 2, denaturate and coagulate the protein content in the dermis 3 and epidermis 1, and thereby decrease the internal adhesion between cells in the dermis and epidermis around the boundary of the PoT 8. A volume of isolated cells 100 containing the affected cells will therefore be formed similar to that illustrated in FIG. 7. After some time, the body will excrete the isolated and disconnected cells 100 as illustrated in FIG. 8. The normal healing process will subsequently replace excreted cells in the dermis 3 and epidermis 2 with new normal cells in FIG. 9.

What is claimed is:

1. An acoustic device comprising:
    a housing with a first end and a longitudinal axis that extends from the first end along a length of the housing;
    a piezoelectric transducer coupled to the housing and comprising a piezoelectric element in the shape of a section of a sphere wherein the piezoelectric element is designed to have a focal zone that at a 6 dB pressure drop from a center of maximum pressure is 1.5 mm or less in diameter and is 3 mm or less along the longitudinal axis;
    a power unit that is in electrical communication with the piezoelectric element and designed to operate the piezoelectric element at a third, or higher, harmonic resonance frequency;
    an optical monitoring system comprising at least one lens with an optical axis aligned with the longitudinal axis and wherein the optical monitoring system is coupled to the housing on an opposite side of the piezoelectric transducer to the first end; and
    an optically transparent pathway that extends along the longitudinal axis from the optical monitoring system, through the piezoelectric transducer including the piezoelectric element, to the first end.

2. The acoustic device of claim 1, wherein the piezoelectric transducer is designed to focus acoustic waves generated by the piezoelectric element to a point of treatment that is between 0.1 mm and 10 mm past the first end.

3. The acoustic device of claim 1, wherein the section of a sphere has a thickness between 0.2 mm and 2 mm.

4. The acoustic device of claim 1, wherein the diameter of the focal zone is 500 μm or less.

5. The acoustic device of claim 1, wherein the power unit is designed to operate the piezoelectric element between 7 MHz and 50 MHz.

6. The acoustic device of claim 1, wherein the power unit is impedance matched to the piezoelectric element and designed to operate the piezoelectric element at a third harmonic resonance frequency.

7. The acoustic device of claim 6, wherein the power unit is designed to drive the piezoelectric element at a parallel resonance frequency.

8. The acoustic device of claim 1 wherein the optically transparent pathway passes through a hole in the center of the piezoelectric element, an acoustic coupling medium retained in a cavity located between the piezoelectric transducer and the first end, and an acoustic window made from an optically transparent material coupled to the first end.

9. The acoustic device of claim 1, wherein the piezoelectric transducer is designed to focus acoustic waves to an acoustic intensity of 1000 W/cm$^2$ or more confined to a diameter of 2 mm or less in the X-Y plane where the Z-axis is parallel to a longitudinal axis of the piezoelectric transducer.

10. The acoustic device of claim 1, further comprising a cavity in the housing between the piezoelectric element and the first end wherein the cavity contains a coupling medium.

11. The acoustic device of claim 10, wherein the coupling medium is water.

12. The acoustic device of claim 1, wherein the housing has a hole in the first end that is covered by an acoustic window.

13. The acoustic device of claim 1, wherein the optical monitoring system is designed to operate with light at a wavelength between 290 nm and 1100 nm.

14. The acoustic device of claim 1, wherein the optical monitoring system comprises an image sensor that is a CCD camera or a CMOS sensor.

15. An acoustic device comprising:
a housing with a first end and a longitudinal axis that extends from the first end along a length of the housing;
a piezoelectric transducer coupled to the housing and comprising a piezoelectric element in the shape of a section of a sphere wherein the piezoelectric element is designed to have a focal zone that at a 6 dB pressure drop from a center of maximum pressure is 1.5 mm or less in diameter and is 3 mm or less along the longitudinal axis;
a power unit that is in electrical communication with the piezoelectric element and designed to operate the piezoelectric element at a third, or higher, harmonic resonance frequency;
an optical monitoring system comprising at least one lens with an optical axis aligned with the longitudinal axis and wherein the optical monitoring system is coupled to the housing on an opposite side of the piezoelectric transducer to the first end; and
an optically transparent pathway that extends entirely along the longitudinal axis from the optical monitoring system through the piezoelectric transducer, including extending through a center of the piezoelectric element, to the first end.

16. The acoustic device of claim 15, wherein the power unit is impedance matched to the piezoelectric element and designed to operate the piezoelectric element at a third harmonic resonance frequency.

17. The acoustic device of claim 16, wherein the power unit is designed to drive the piezoelectric element at a parallel resonance frequency.

18. The acoustic device of claim 17, wherein the spherical section has a thickness between 0.2 mm and 2 mm.

* * * * *